(12) United States Patent
Schraga et al.

(10) Patent No.: US 9,017,356 B2
(45) Date of Patent: Apr. 28, 2015

(54) MULTI-LANCET UNIT, METHOD AND LANCET DEVICE USING THE MULTI-LANCET UNIT, AND METHOD OF ASSEMBLING AND/OR MAKING THE MULTI-LANCET UNIT

(75) Inventors: Steven Schraga, Surfside, FL (US); Paul R. Fuller, Denvers, MA (US); Brian Schwartz, Lake in the Hills, IL (US); David A. Carhart, Drive Cary, IL (US)

(73) Assignee: Stat Medical Devices, Inc., North Miami Beach, FL (US)

( * ) Notice: Subject to any disclaimer, the term of this patent is extended or adjusted under 35 U.S.C. 154(b) by 1291 days.

(21) Appl. No.: 12/525,982

(22) PCT Filed: Feb. 8, 2008

(86) PCT No.: PCT/US2008/053400
§ 371 (c)(1),
(2), (4) Date: Mar. 15, 2011

(87) PCT Pub. No.: WO2008/100818
PCT Pub. Date: Aug. 21, 2008

(65) Prior Publication Data
US 2011/0160759 A1   Jun. 30, 2011

Related U.S. Application Data

(60) Provisional application No. 60/900,349, filed on Feb. 9, 2007.

(51) Int. Cl.
*A61B 17/32* (2006.01)
*A61B 5/15* (2006.01)
*A61B 5/151* (2006.01)

(52) U.S. Cl.
CPC ........... *A61B 5/1411* (2013.01); *A61B 5/15146* (2013.01)

(58) Field of Classification Search
CPC ............... A61B 5/151; A61B 5/15101; A61B 5/15103; A61B 5/15105; A61B 5/15107; A61B 5/15109; A61B 5/15111; A61B 5/15113; A61B 5/15115; A61B 5/15117; A61B 5/15126; A61B 5/15128; A61B 5/1513; A61B 5/15132; A61B 5/1411
USPC .................................. 606/181–183; 600/583
See application file for complete search history.

(56) References Cited

U.S. PATENT DOCUMENTS

| 676,678 A | 6/1901 | Ellifrits |
|---|---|---|
| 1,135,465 A | 4/1915 | Pollock |

(Continued)

FOREIGN PATENT DOCUMENTS

| CA | 523 078 | 3/1956 |
|---|---|---|
| EP | 0 061 102 | 3/1982 |

(Continued)

OTHER PUBLICATIONS

Sutor et al., "Bleeding from Standardized Skin Punctures: Automated Technic for Recording Time, Intensity, and Pattern of Bleeding", *A.J.C.P.*, vol. 55, pp. 541-549 (May 1971).

*Primary Examiner* — Thomas McEvoy
(74) *Attorney, Agent, or Firm* — Greenblum & Bernstein, P.L.C.

(57) ABSTRACT

A lancet device includes a housing, a trigger, a system for placing the lancet device in a trigger-set or armed position, and a multi-lancet unit comprising a plurality of lancets arranged one in front of the other and positioned in the housing. Each lancet includes a front end, a needle which extends from the front end, and a rear end. The front end of at least one of the plurality lancets is removably connected to the rear end of another of the plurality of lancets. A method of puncturing a surface of skin using the lancet device includes arranging the lancet device adjacent against a user's skin and triggering the lancet device so that one of the plurality of lancet is caused to penetrate the user's skin.

35 Claims, 28 Drawing Sheets

(56) References Cited

U.S. PATENT DOCUMENTS

| | | | |
|---|---|---|---|
| 2,699,784 | A | 1/1955 | Krayl |
| 2,848,809 | A | 8/1958 | Crowder |
| 3,030,959 | A | 4/1962 | Grunert |
| 3,589,213 | A | 6/1971 | Gourley |
| 4,139,011 | A | 2/1979 | Benoit et al. |
| 4,203,446 | A | 5/1980 | Hofert et al. |
| 4,257,561 | A | 3/1981 | McKinney |
| 4,388,925 | A | 6/1983 | Burns |
| 4,426,105 | A | 1/1984 | Plaquin et al. |
| 4,449,529 | A | 5/1984 | Burns et al. |
| 4,469,110 | A | 9/1984 | Slama |
| 4,517,978 | A | 5/1985 | Levin et al. |
| 4,527,561 | A | 7/1985 | Burns |
| 4,628,929 | A | 12/1986 | Integan et al. |
| 4,785,858 | A | 11/1988 | Valentini et al. |
| RE32,922 | E | 5/1989 | Levin et al. |
| 4,834,667 | A | 5/1989 | Fowler et al. |
| 4,858,607 | A | 8/1989 | Jordan et al. |
| 4,869,249 | A | 9/1989 | Crossman et al. |
| 4,895,147 | A | 1/1990 | Bodicky et al. |
| 4,924,879 | A | 5/1990 | O'Brien |
| 4,976,724 | A | 12/1990 | Nieto et al. |
| 4,990,154 | A | 2/1991 | Brown et al. |
| 5,074,872 | A | 12/1991 | Brown et al. |
| 5,147,375 | A | 9/1992 | Sullivan et al. |
| 5,212,879 | A | 5/1993 | Biro et al. |
| 5,269,799 | A | 12/1993 | Daniel |
| 5,282,822 | A | 2/1994 | Macors et al. |
| 5,304,193 | A | 4/1994 | Zhadanov |
| 5,318,584 | A | 6/1994 | Lange et al. |
| 5,324,303 | A | 6/1994 | Strong et al. |
| 5,350,392 | A | 9/1994 | Purcell et al. |
| 5,356,420 | A | 10/1994 | Czernecki et al. |
| 5,366,470 | A | 11/1994 | Ramel |
| 5,395,388 | A | 3/1995 | Schraga |
| 5,423,847 | A | 6/1995 | Strong et al. |
| 5,439,473 | A | 8/1995 | Jorgensen |
| 5,454,828 | A | 10/1995 | Schraga |
| 5,464,418 | A | 11/1995 | Schraga |
| 5,476,101 | A | 12/1995 | Schramm et al. |
| 5,487,748 | A | 1/1996 | Marshall et al. |
| 5,509,345 | A | 4/1996 | Cyktich |
| 5,518,004 | A | 5/1996 | Schraga |
| 5,554,166 | A | 9/1996 | Lange et al. |
| 5,569,286 | A | 10/1996 | Peckham et al. |
| 5,569,287 | A | 10/1996 | Tezuka et al. |
| D376,203 | S | 12/1996 | Schraga |
| 5,613,978 | A | 3/1997 | Harding |
| 5,628,764 | A | 5/1997 | Schraga |
| 5,628,765 | A | 5/1997 | Morita |
| 5,643,306 | A | 7/1997 | Schraga |
| 5,730,753 | A | 3/1998 | Morita |
| 5,741,288 | A | 4/1998 | Rife |
| RE35,803 | E | 5/1998 | Lange et al. |
| 5,797,942 | A | 8/1998 | Schraga |
| 5,873,887 | A | 2/1999 | King et al. |
| 5,879,367 | A | 3/1999 | Latterell et al. |
| 5,908,434 | A | 6/1999 | Schraga |
| 5,916,230 | A | 6/1999 | Brenneman et al. |
| 5,984,940 | A | 11/1999 | Davis et al. |
| 6,022,366 | A | 2/2000 | Schraga |
| 6,045,567 | A | 4/2000 | Taylor et al. |
| 6,056,765 | A | 5/2000 | Bajaj et al. |
| 6,071,294 | A | 6/2000 | Simons et al. |
| D428,150 | S | 7/2000 | Ruf et al. |
| 6,136,013 | A | 10/2000 | Marshall et al. |
| 6,152,942 | A | 11/2000 | Brenneman et al. |
| 6,156,050 | A | 12/2000 | Davis et al. |
| 6,156,051 | A | 12/2000 | Schraga |
| 6,161,976 | A | 12/2000 | Liu |
| 6,168,606 | B1 | 1/2001 | Levin et al. |
| 6,183,489 | B1 | 2/2001 | Douglas et al. |
| 6,190,398 | B1 | 2/2001 | Schraga |
| 6,192,891 | B1 | 2/2001 | Gravel et al. |
| 6,197,040 | B1 | 3/2001 | LeVaughn et al. |
| 6,210,420 | B1 | 4/2001 | Mauze et al. |
| 6,221,089 | B1 | 4/2001 | Mawhirt |
| 6,228,100 | B1 | 5/2001 | Schraga |
| 6,258,112 | B1 | 7/2001 | Schraga |
| 6,283,982 | B1 | 9/2001 | Levaughn et al. |
| 6,306,152 | B1 | 10/2001 | Verdonk et al. |
| 6,322,574 | B1 | 11/2001 | Lloyd et al. |
| 6,322,575 | B1 | 11/2001 | Schraga |
| 6,332,871 | B1 | 12/2001 | Douglas et al. |
| 6,346,114 | B1 | 2/2002 | Schraga |
| 6,364,889 | B1 | 4/2002 | Kheiri et al. |
| 6,379,317 | B1 | 4/2002 | Kintzig et al. |
| 6,409,740 | B1 | 6/2002 | Kuhr et al. |
| 6,419,661 | B1 | 7/2002 | Kuhr et al. |
| 6,451,040 | B1 | 9/2002 | Purcell |
| 6,464,649 | B1 | 10/2002 | Duchon et al. |
| 6,506,168 | B1 | 1/2003 | Fathallah et al. |
| 6,514,270 | B1 | 2/2003 | Schraga |
| 6,540,762 | B1 | 4/2003 | Bertling |
| 6,558,402 | B1 | 5/2003 | Chelak et al. |
| 6,645,219 | B2 | 11/2003 | Roe |
| 2002/0077650 | A1 | 6/2002 | Schraga |
| 2003/0050656 | A1 | 3/2003 | Schraga |
| 2006/0173478 | A1 | 8/2006 | Schraga |
| 2006/0229652 | A1 | 10/2006 | Iio et al. |
| 2006/0241668 | A1 | 10/2006 | Schraga |

FOREIGN PATENT DOCUMENTS

| | | |
|---|---|---|
| EP | 0 137 975 | 8/1984 |
| EP | 0 189 117 | 1/1986 |
| EP | 0 904 731 | 9/1998 |
| EP | 0 885 590 | 12/1998 |
| EP | 1 074 219 | 7/2000 |
| FR | 1 126 718 | 6/1955 |
| FR | 2 797 579 | 8/1999 |
| KR | 10-2001-0020623 | 1/2000 |
| WO | 93/19671 | 10/1993 |

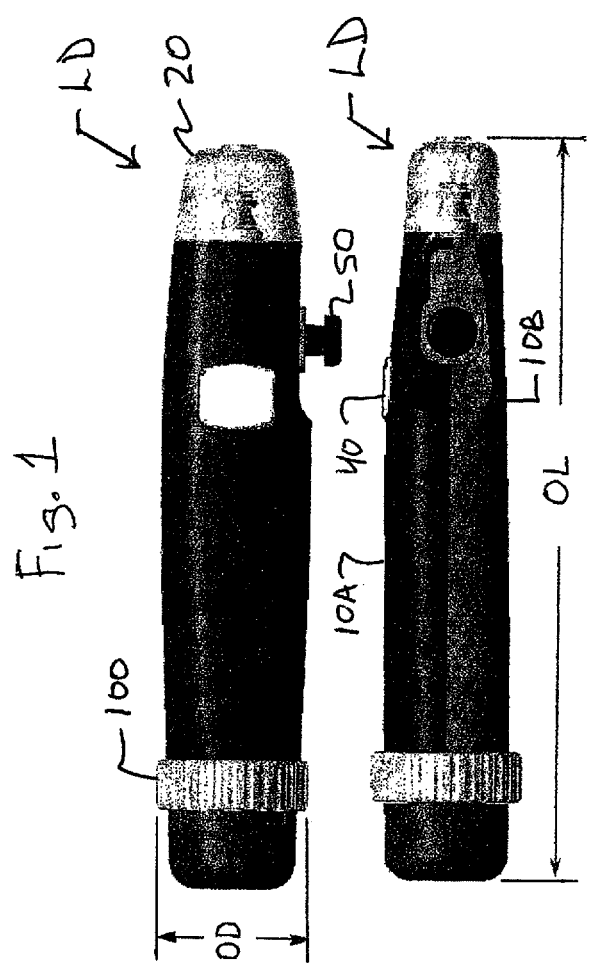

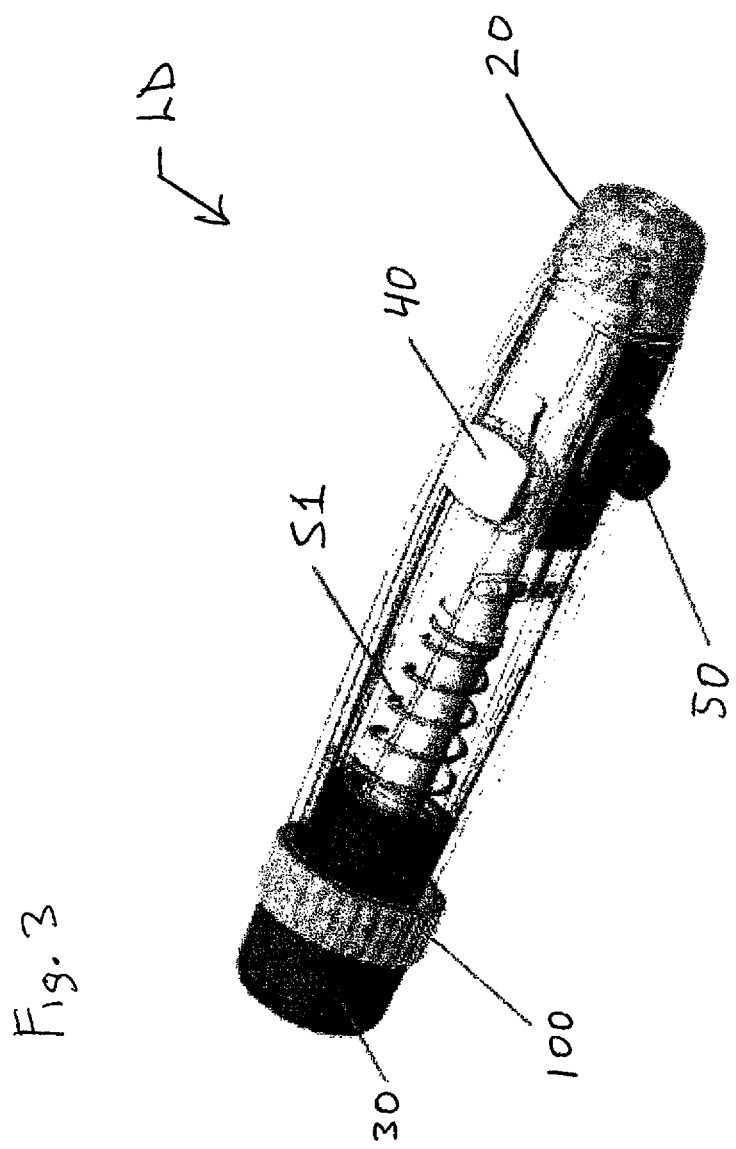

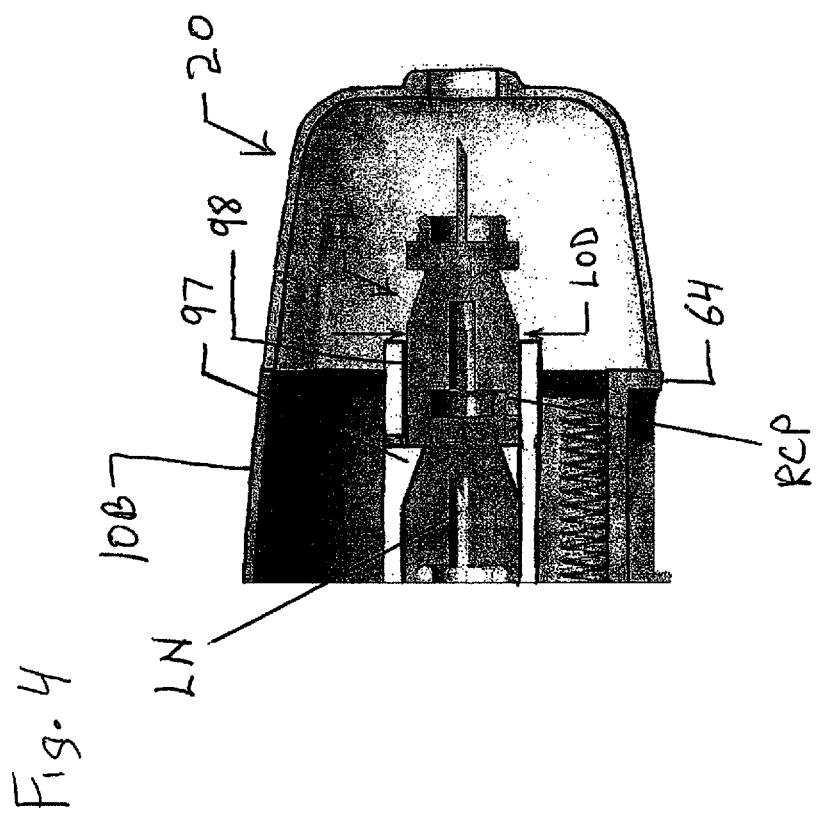

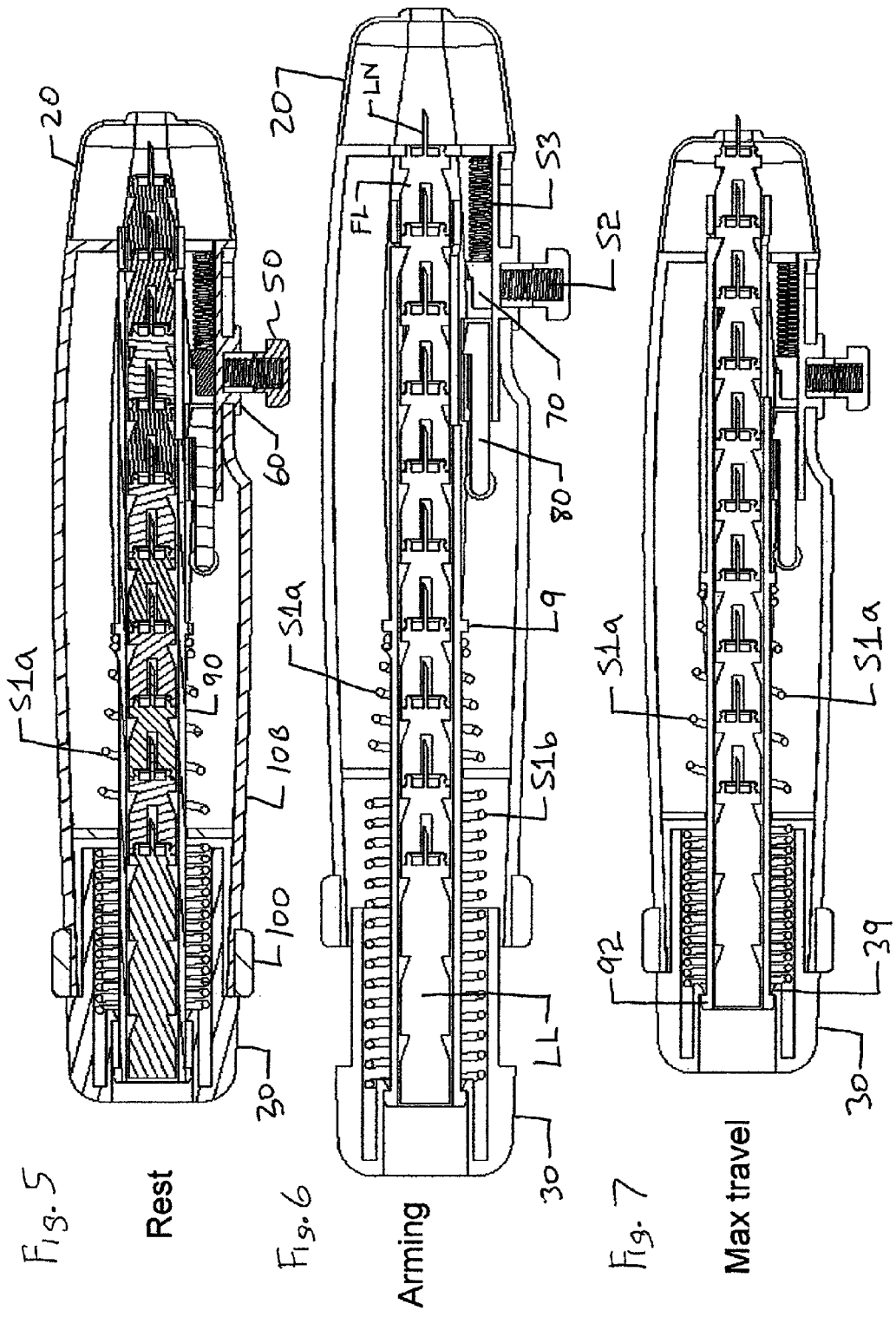

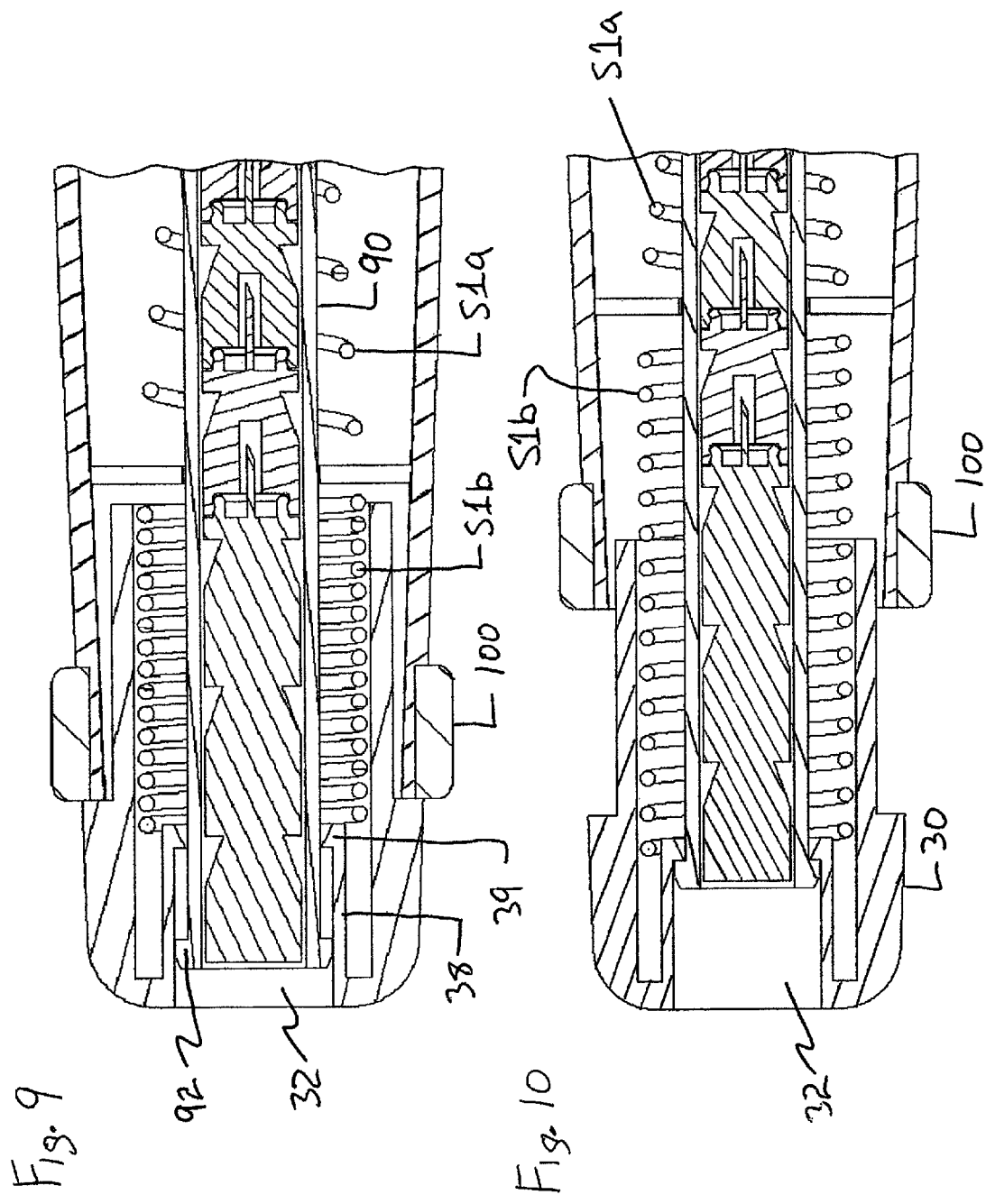

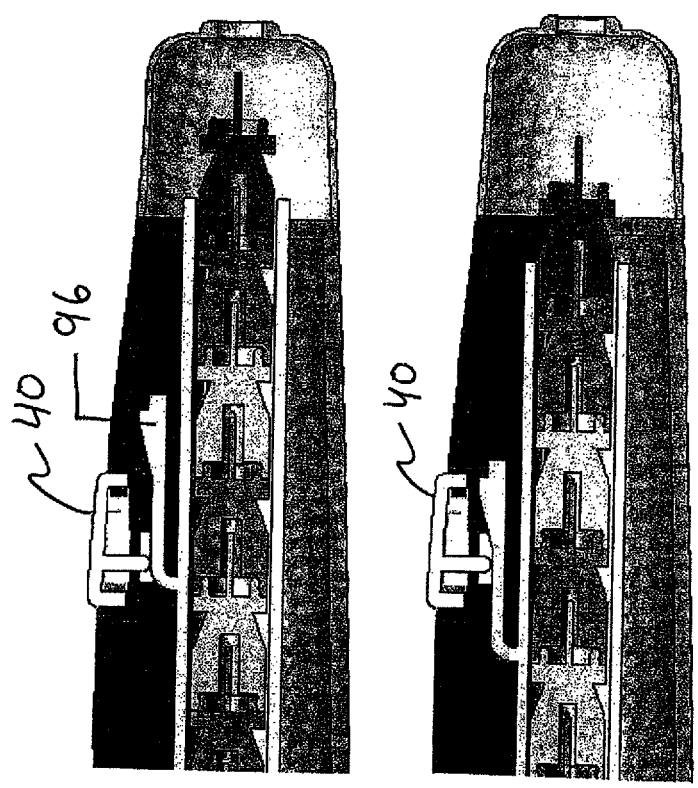

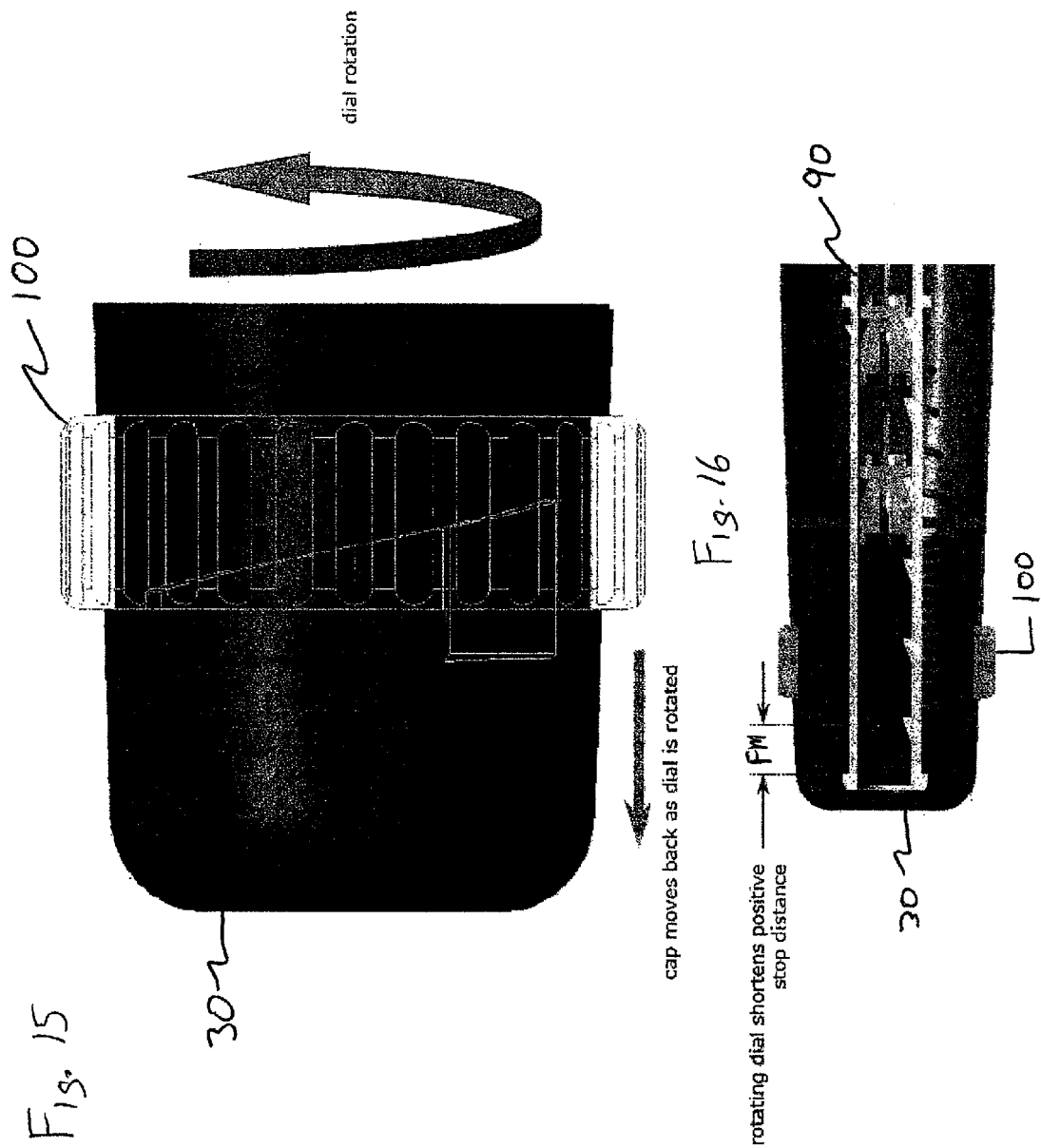

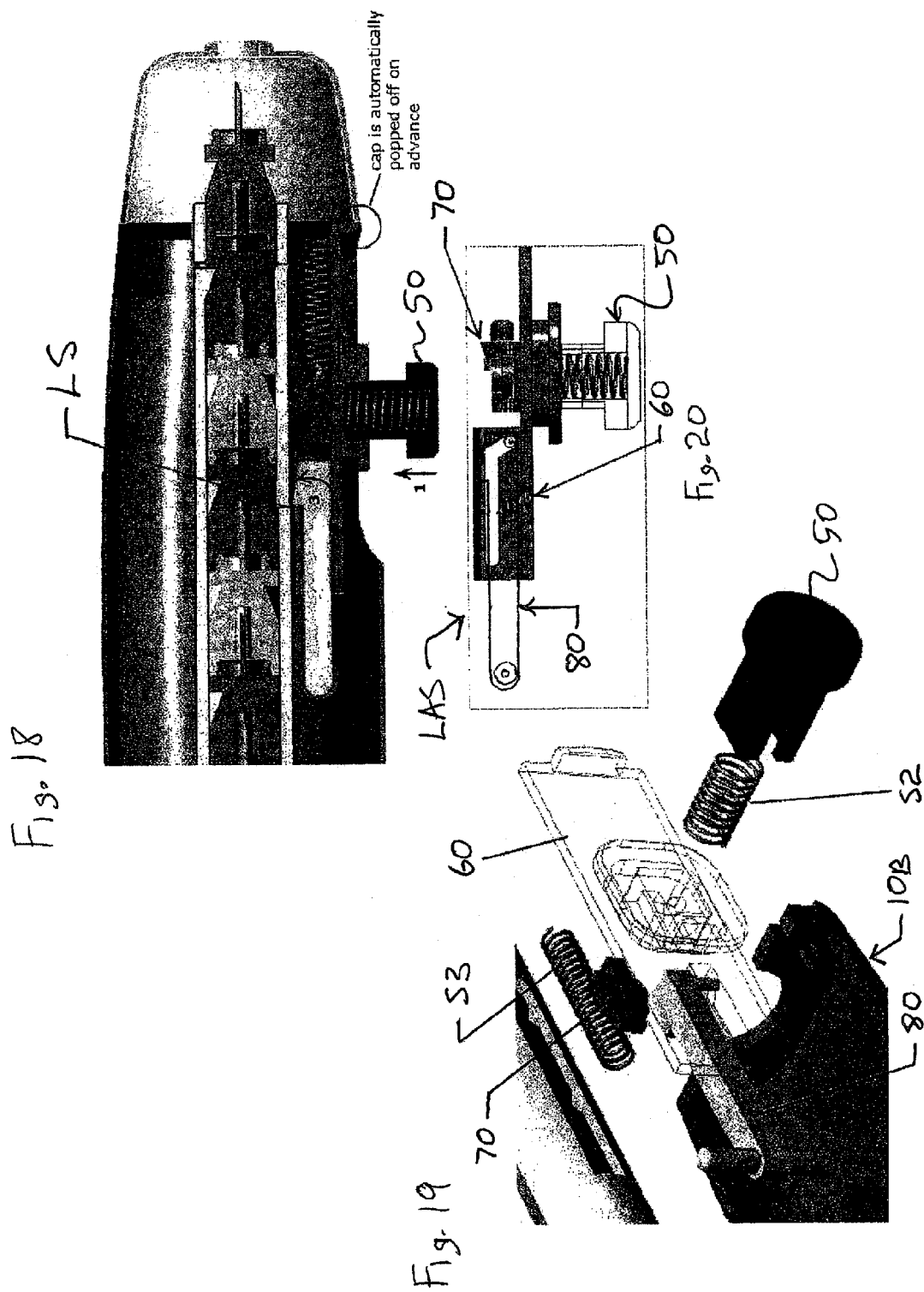

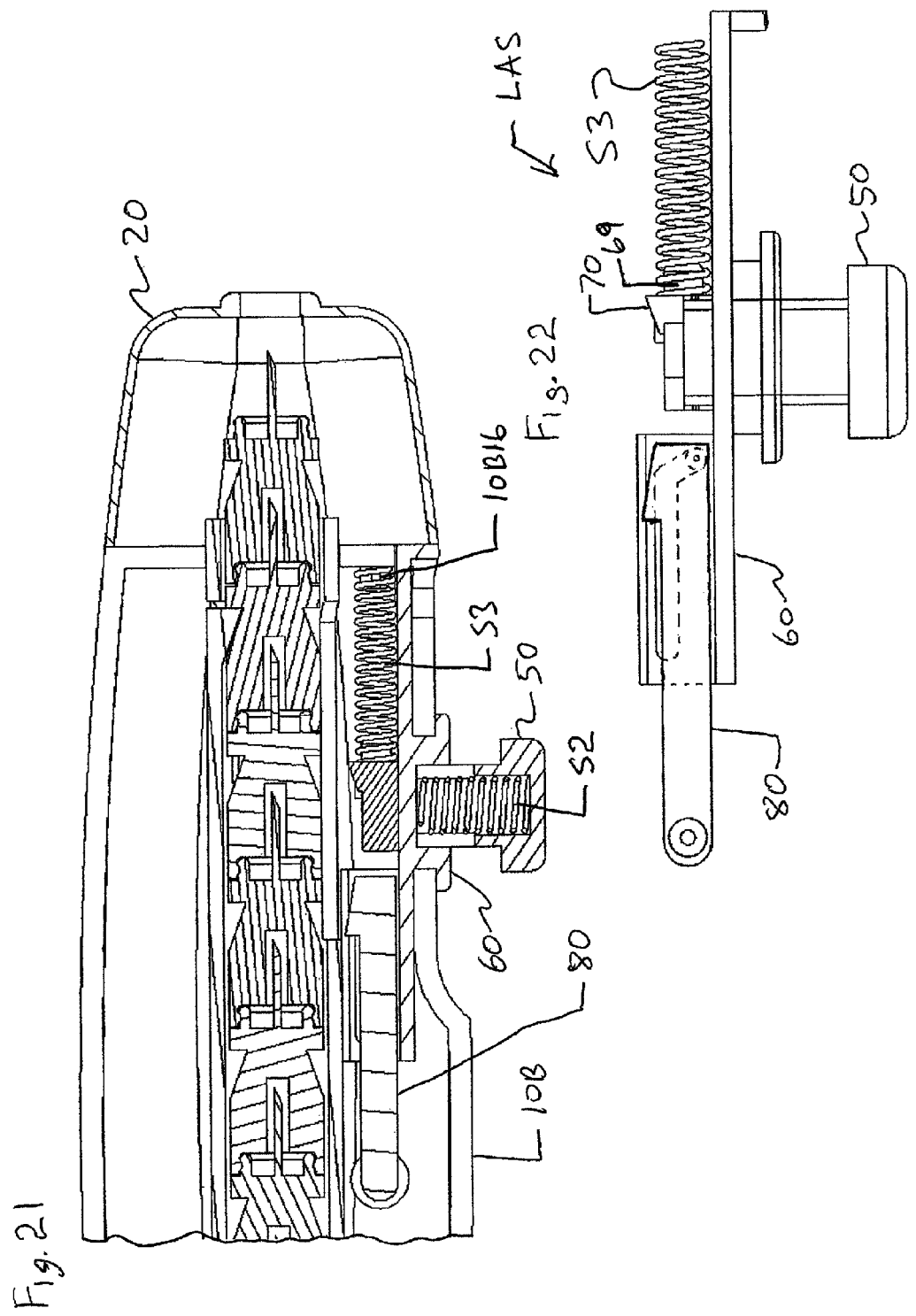

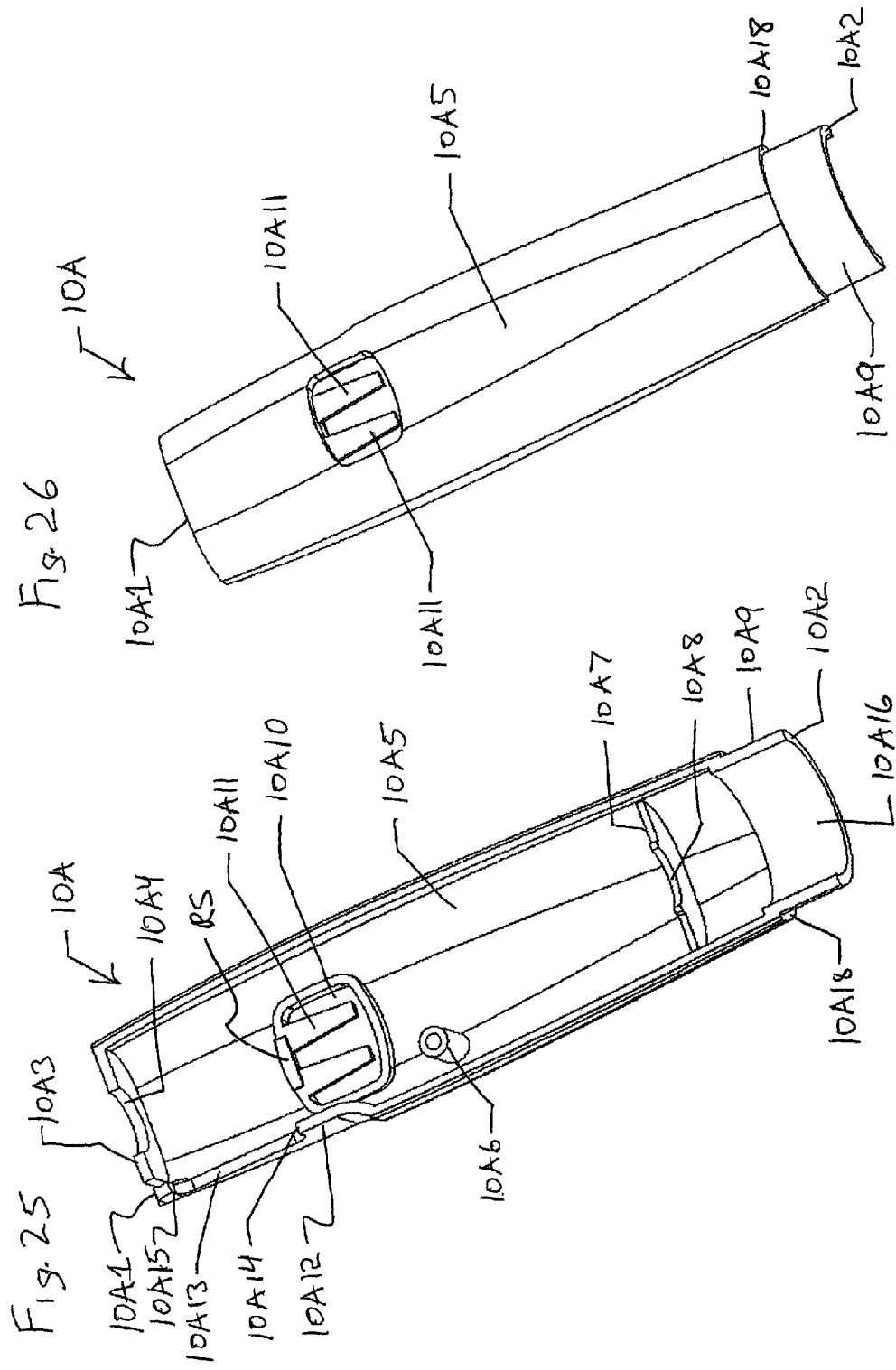

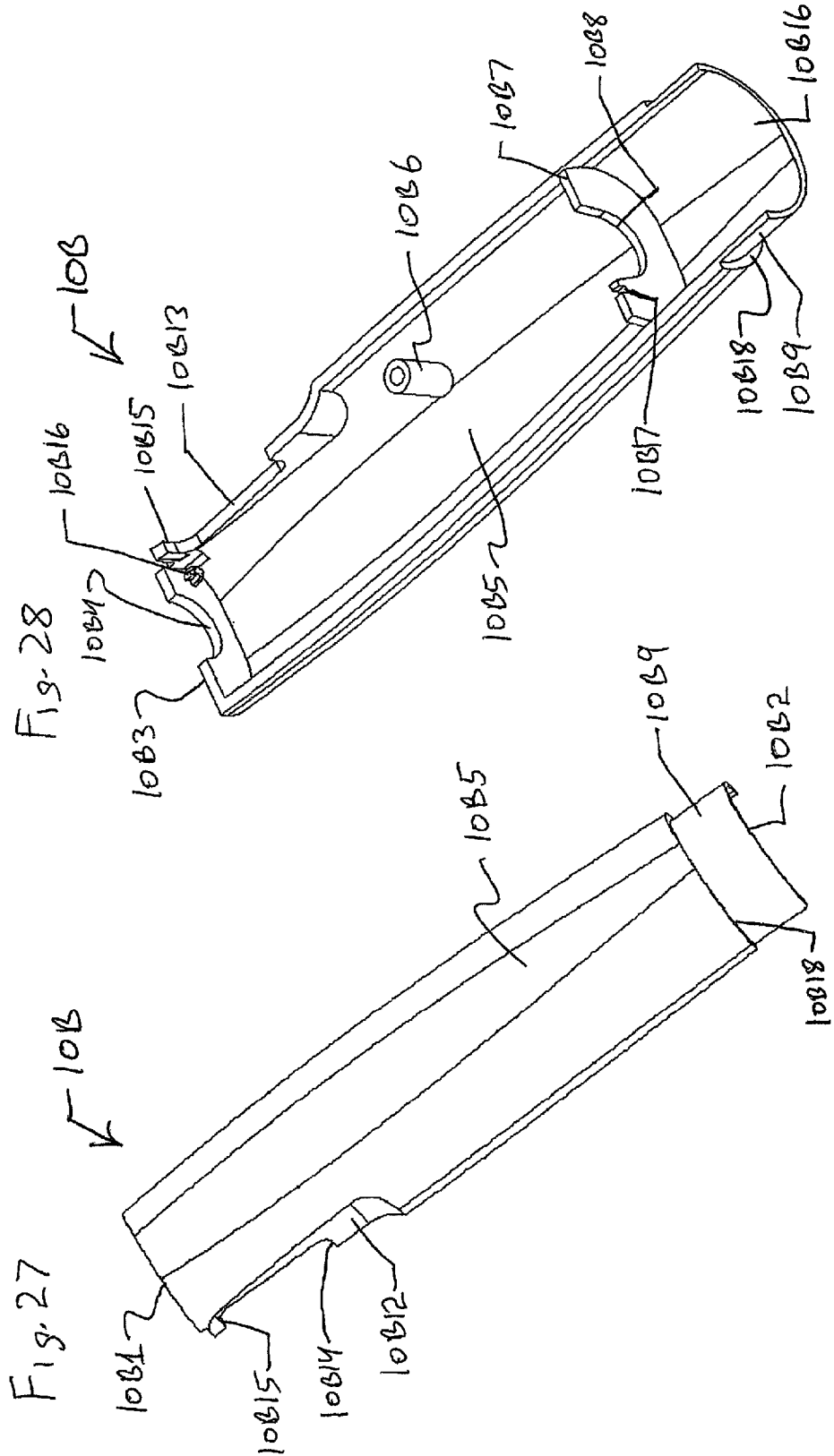

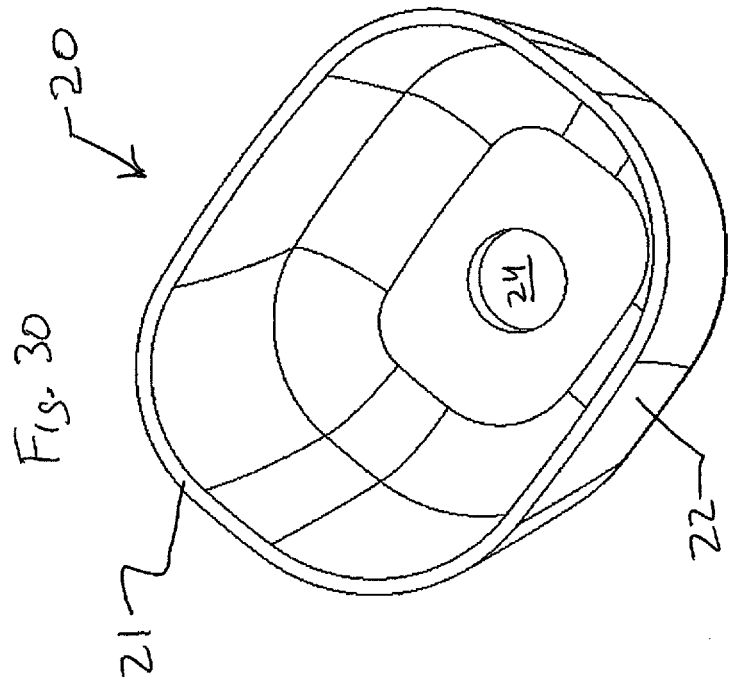
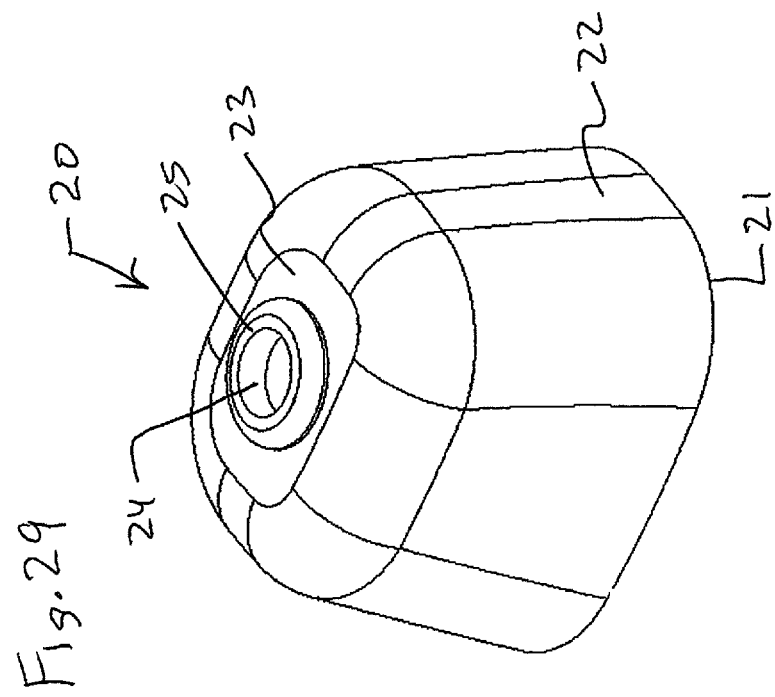

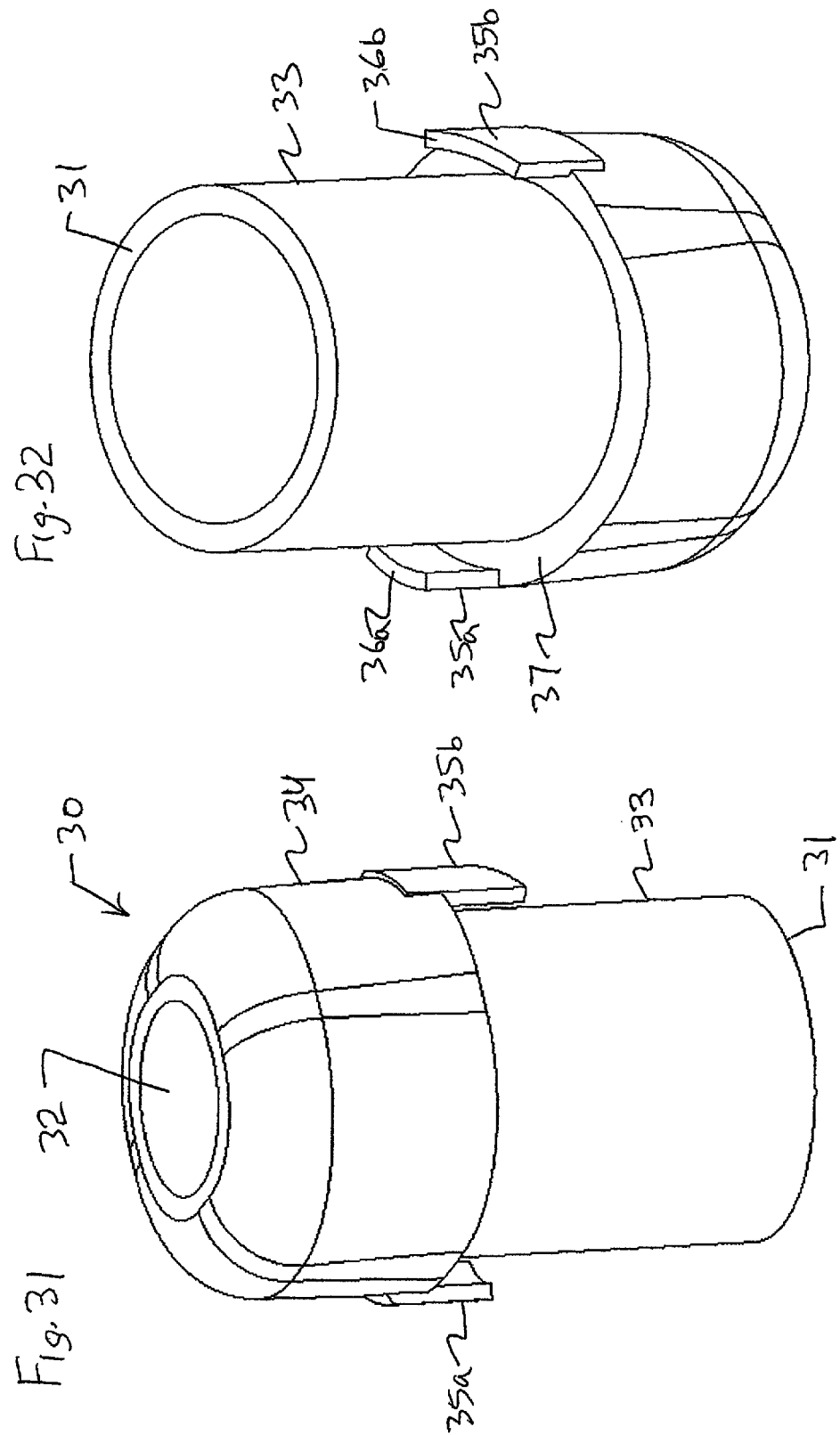

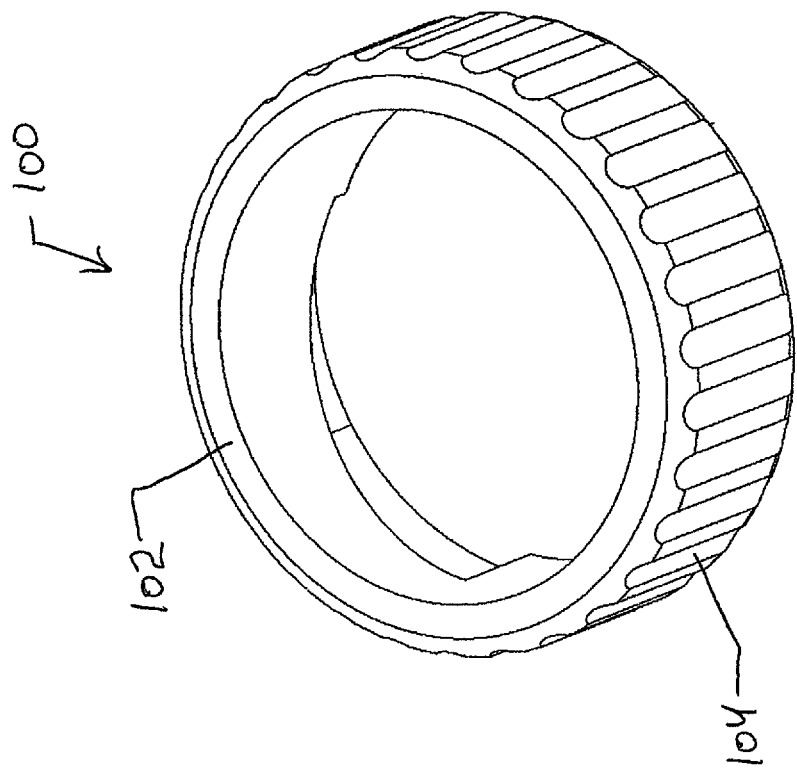
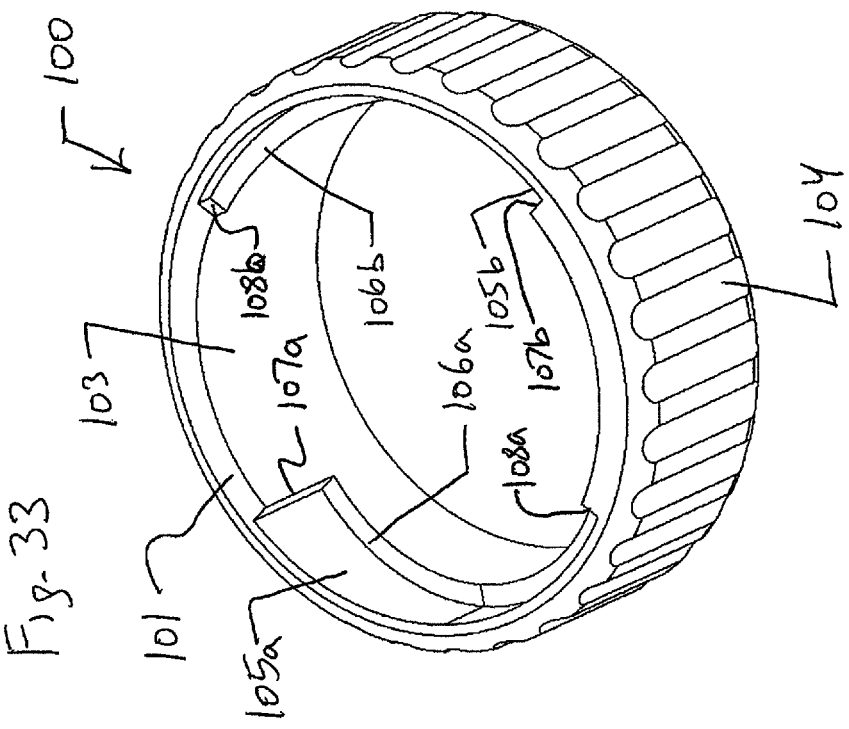

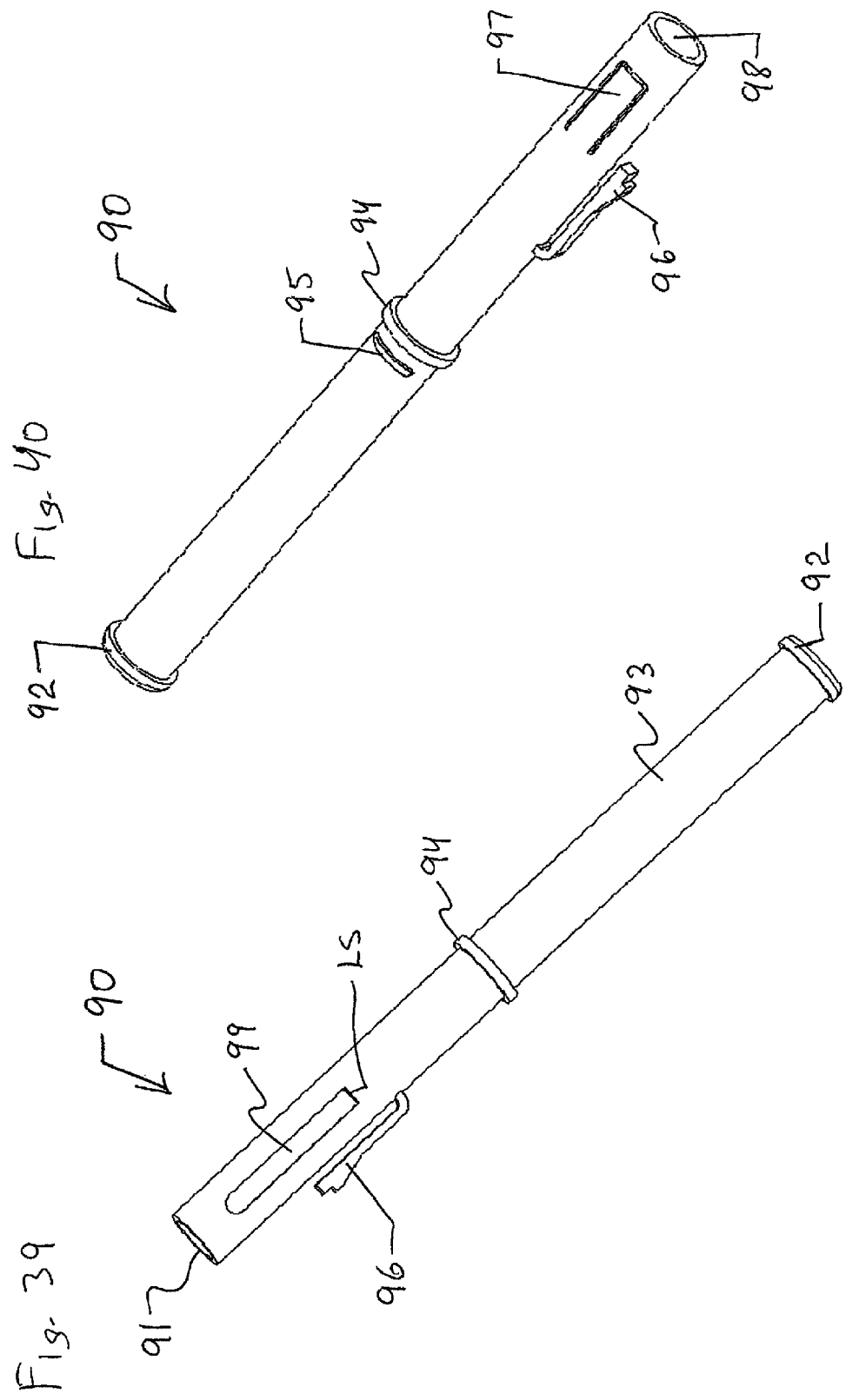

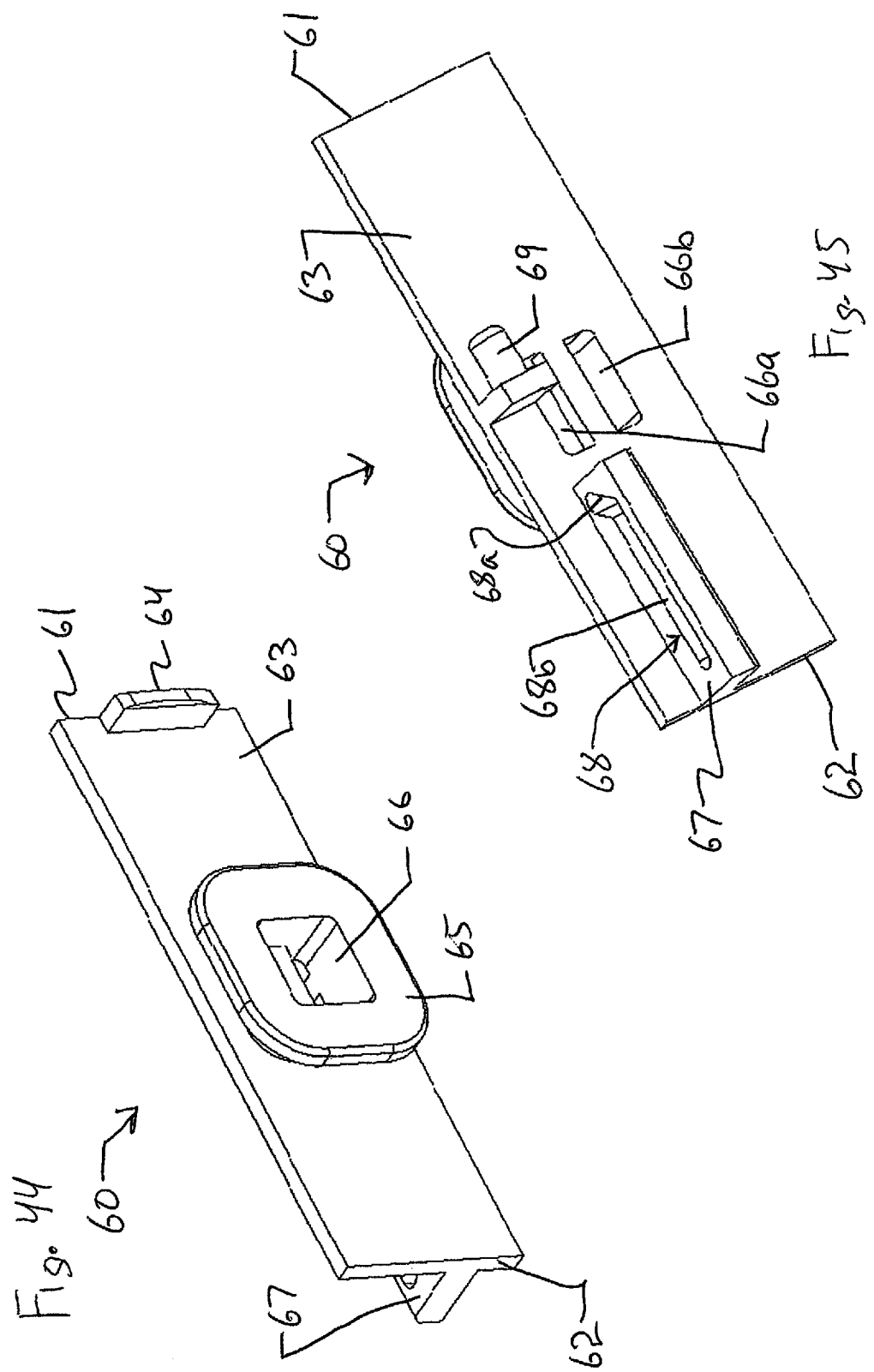

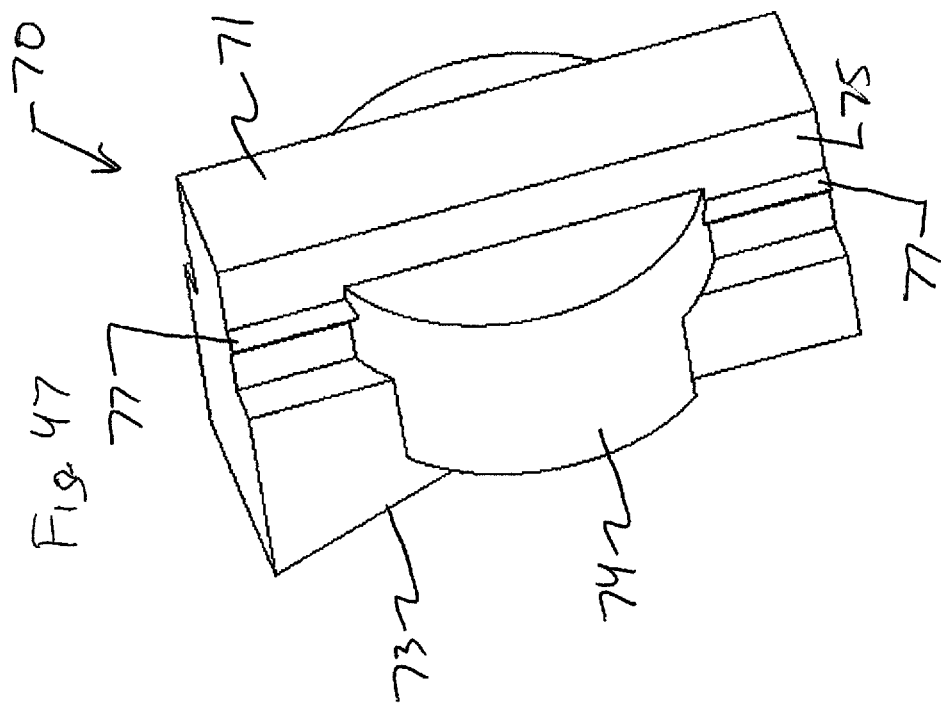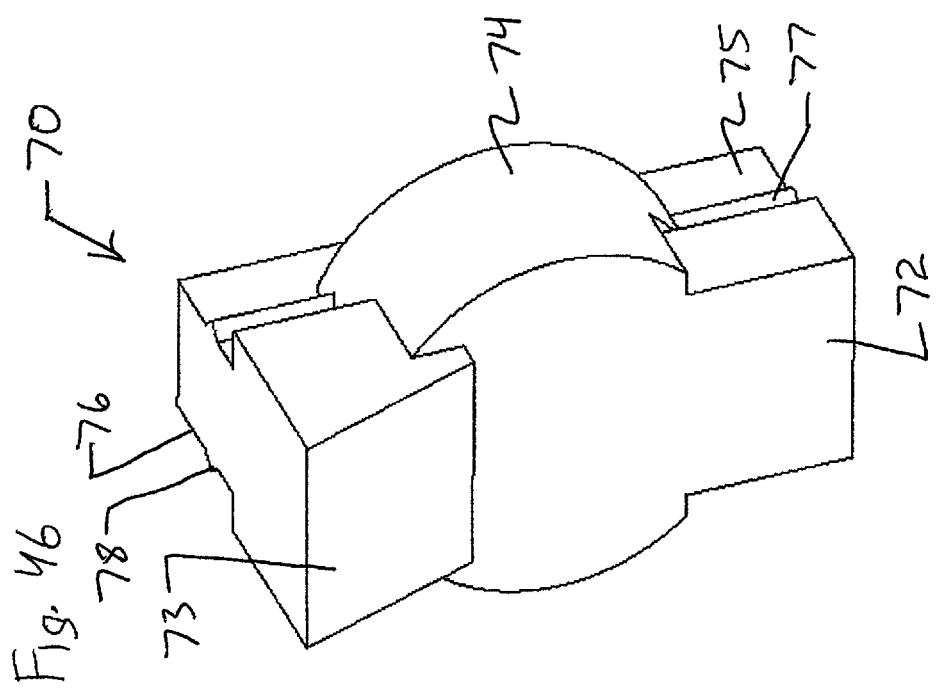

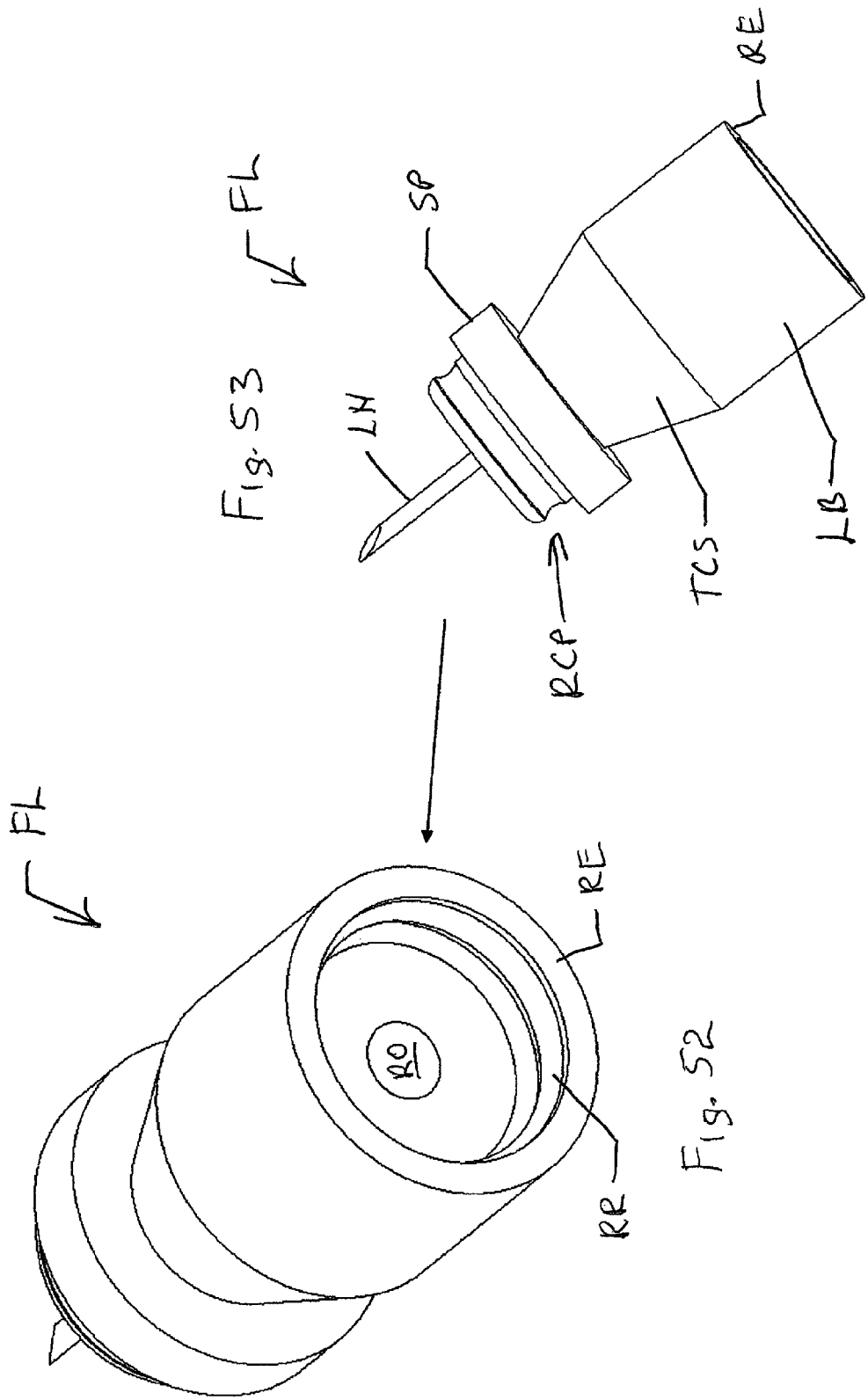

MULTI-LANCET UNIT, METHOD AND LANCET DEVICE USING THE MULTI-LANCET UNIT, AND METHOD OF ASSEMBLING AND/OR MAKING THE MULTI-LANCET UNIT

CROSS-REFERENCE TO RELATED APPLICATIONS

The instant application is a U.S. National Stage of International Application No. PCT/US2008/053400 filed Feb. 8, 2008 which published as WO 2008/100818 on Aug. 21, 2008, claims the benefit of U.S. provisional application No. 60/900, 349, filed Feb. 9, 2007, the disclosure of each of these documents is hereby expressly incorporated by reference hereto in their entireties.

BACKGROUND OF THE INVENTION

1. Field of the Invention

The invention relates to a lancet device which utilizes a multi-lancet unit having the form of lancets arranged in serried and/or one in front of the other. Lancet devices are used to penetrate and puncture the skin in order to allow the taking of a blood sample for testing. The present device allows the user to use the device a number of times without having to reinstall a lancet after each use.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like.

What is needed is a lancet device which does not require the user to handle the lancets (or which minimizes handling of the lancets) so as to prevent inadvertent pricking of the user's skin. What is also needed is a lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices.

Thus, while advances have been made, there is a continuing need for a lancet device which provides for convenient, reliable and easy adjustment of penetration depth. There is also a need for lancet device which includes plural lancets which can be replaced and/or a device which can be disposed of after all of the lancets are used.

SUMMARY OF THE INVENTION

According to one illustrative aspect of the invention there is provided a lancet device comprising a housing, a trigger, a system for placing the lancet device in a trigger-set or armed position, and a multi-lancet unit comprising a plurality of lancets arranged one in front of the other and positioned in the housing. Each lancet comprises a front end, a needle which extends from the front end, and a rear end. The front end of at least one of the plurality lancets is removably connected to the rear end of another of the plurality of lancets.

The plurality of lancets may comprise two lancets. The plurality of lancets may comprise at least three lancets. The plurality of lancets may be between five lancets and twenty lancets. The plurality of lancets may be between eight lancets and twelve lancets. Each of the plurality of lancets may comprise a generally cylindrical portion. Each of the plurality of lancets may comprise a generally circular cross-section when viewed perpendicular to a center axis of the plurality of lancets. At least one of the plurality of lancets may comprise a locking mechanism. The locking mechanism may be at least one of a circumferential locking recess and a tapered recess. Each of the plurality of lancets may comprise a locking recess.

The lancet device may further comprise a depth adjustment system. The lancet device may further comprise a depth adjustment system and a holding member which houses the multi-lancet unit. The lancet device may further comprise a movable holding member which is configured to receive the multi-lancet unit and a rotatably mounted depth adjustment element. The lancet device may further comprise at least one of a system for removing or ejecting a lancet of the plurality of lancets and a system for advancing or positioning an unused lancet into a position previously held by a used lancet that has been removed. The lancet device may further comprise a manually activated system for removing or ejecting a used lancet of the multi-lancet unit. The lancet device may further comprise a system for removing or ejecting a used lancet of the multi-lancet unit and for causing removal of a front cap.

The invention also provides for a method of puncturing a surface of skin using the lancet device of any of the types described herein, wherein the method comprises arranging the lancet device adjacent against a user's skin and triggering the lancet device so that one of the plurality of lancet is caused to penetrate the user's skin.

The invention also provides for a lancet device comprising a housing, a trigger, a depth adjustment system, and a plurality of lancets arranged one in front of the other and positioned in the housing. Each lancet comprises a front end, a needle which extends from the front end, and a rear end. The front end of at least one of the plurality lancets is removably connected to the rear end of another of the plurality of lancets.

The plurality of lancets may comprise at least three lancets. The plurality of lancets may be between eight lancets and twelve lancets. Each of the plurality of lancets may comprise a generally cylindrical portion. The lancet device may further comprise a system for placing the lancet device in a trigger-set or armed position. The lancet device may further comprise a holding member which houses the plurality of lancets. The plurality of lancets may comprise a multi-lancet unit and further comprising a system for removing or ejecting a lancet of the multi-lancet unit. The plurality of lancets may comprise a multi-lancet unit and further comprising a manually activated system for removing or ejecting a used lancet of the multi-lancet unit. The plurality of lancets may comprise a multi-lancet unit and further comprising a system for removing or ejecting a used lancet of the multi-lancet unit and for causing removal of a front cap.

The invention also provides a method of puncturing a surface of skin using the lancet device of the type described herein, wherein the method comprises arranging the lancet device adjacent against a user's skin and triggering the lancet device so that one of the plurality of lancet is caused to penetrate the user's skin.

The invention also provides for a lancet device comprising a trigger, a depth adjustment system, a system for placing the lancet device is a trigger-set position, a plurality of lancets arranged one in front of the other, a multi-lancet unit comprising a plurality of lancets arranged one in front of the other and a system for axially moving or advancing the multi-lancet unit.

The invention also provides for a lancet device comprising at least one, preferably most, and most preferably all of the features shown in the drawings of the instant application.

The invention also provides for a multi-lancet unit comprising a plurality of lancets arranged one in front of the other and positioned in the housing. A first lancet comprises a front end, a needle which extends from the front end, and a rear opening sized to receive therein a lancet needle of a second lancet arranged behind the first lancet. The first and second lancets are connected together via at least one of a releasable snap connection and a connection formed by frictional engagement between an annular flange of the second lancet and a recess arranged in a rear end of the first lancet Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 1 shows a left side view of a non-limiting embodiment of the invention;

FIG. 2 shows a top side view of FIG. 1;

FIG. 3 shows a perspective view of the device shown in FIGS. 1 and 2 with the body portion being shown transparent in order to illustrate the inner workings of the device;

FIG. 4 shows an enlarged cross-section view of a front portion of the lancet device shown in FIG. 1;

FIG. 5 shows a side cross-section view of FIG. 1. The device is shown in an initial or intermediate state;

FIG. 6 shows a side cross-section view of FIG. 5 (cross-hatching removed for purposes of clarity) after the device is placed in an arming or trigger-set position;

FIG. 7 shows a side cross-section view of FIG. 6 after the device is triggered and before the lancet holding member is automatically moved back to the position shown in FIG. 5;

FIG. 9 shows an enlarged cross-section view of a rear portion of the lancet device shown in FIGS. 1-3. The arming back cap is shown in an initial position;

FIG. 10 shows the enlarged cross-section view of FIG. 9 with the arming back cap shown in an arming position;

FIG. 13 shows a front portion of the lancet device shown in FIG. 8 with the lancet device being in an initial or intermediate position;

FIG. 14 shows the front portion of FIG. 13 with the lancet device being in an armed or trigger-set position;

FIG. 15 shows a rear portion of the lancet device with the depth adjustment member being shown transparent and illustrating how one of the projecting members of the back cap engages with one of the tapered recesses of the depth adjustment thumb wheel;

FIG. 16 shows an enlarged cross-section view of a rear portion of the lancet device and illustrates the adjustable distance which controls the depth of penetration of the lancet needle;

FIG. 18 shows an enlarged cross-section view of a front portion of the lancet device shown in FIG. 1 and illustrates the three steps utilized for advancing the multi-lancet unit within the lancet holding member. In step 1, the advance button is depressed so that a lancet engaging member engages with a third lancet. In step 2, the advance button is slid forward slightly to cause the slide plate to slide in the forward direction. This initial forward movement automatically causes the locking member to pivot and engage with a shoulder of the lancet holding member in step 3. Continued forward sliding movement of the slide plate causes the multi-lancet unit to move or advance forwards while the lancet holding member is axially retained by the locking member;

FIG. 19 shows an exploded view of the system for advancing the multi-lancet unit and shows a portion of the lower housing, a portion of the lancet holding member, as well as the advance button, the lancet engaging member, the slide plate (shown transparent for purposes of illustration), the locking member, the advance button spring, and the slide return spring;

FIG. 20 shows an assembled view of the system for advancing the multi-lancet unit and shows the advance button (shown transparent for purposes of illustration), the lancet engaging member, the slide plate, the locking member and the advance button spring;

FIG. 21 shows an enlarged cross-section view of a front portion of the lancet device shown in FIG. 1 and illustrates the system for advancing the multi-lancet unit within the lancet holding member in an initial position;

FIG. 22 shows an assembled side view of the system for advancing the multi-lancet unit shown in FIG. 21;

FIG. 25 shows a perspective inside view of the upper or left-side housing part used in the two-piece housing of the lancet device shown in FIGS. 1-3;

FIG. 26 shows a perspective outside view of the upper or left-side housing part shown in FIG. 25;

FIG. 27 shows a perspective outside view of the lower or right-side housing part used in the two-piece housing of the lancet device shown in FIGS. 1-3;

FIG. 28 shows a perspective inside view of the lower or right-side housing part shown in FIG. 27;

FIG. 29 shows a perspective front side view of the front cap used in the lancet device shown in FIGS. 1-3;

FIG. 30 shows a perspective inside view of the front cap shown in FIG. 29;

FIG. 31 shows a perspective rear side view of the back cap used in the lancet device shown in FIGS. 1-3;

FIG. 32 shows a perspective inside view of the back cap shown in FIG. 31;

FIG. 33 shows a perspective rear side view of the thumb wheel used in the lancet device shown in FIGS. 1-3;

FIG. 34 shows a perspective front side view of the thumb wheel shown in FIG. 33;

FIG. 39 shows a perspective rear side view of the lancet holding member used in the lancet device shown in FIGS. 1-3;

FIG. 40 shows a perspective front view of the lancet holding member shown in FIG. 39;

FIG. 44 shows a perspective top side view of the slide plate used in the lancet device shown in FIGS. 1-3;

FIG. 45 shows a perspective inside view of the slide plate shown in FIG. 44;

FIG. 46 shows a perspective top side view of the lancet engaging member used in the lancet device shown in FIGS. 1-3;

FIG. 47 shows a perspective bottom side view of the lancet engaging member shown in FIG. 46;

FIG. 52 shows a perspective rear side view of the first lancet (as well as all of the other lancets except the last lancet) of the multi-lancet unit used in the lancet device shown in FIGS. 1-3; and FIG. 53 shows a perspective side view of the first lancet shown in FIG. 52.

DETAILED DESCRIPTION OF THE PRESENT INVENTION

Figure 8:
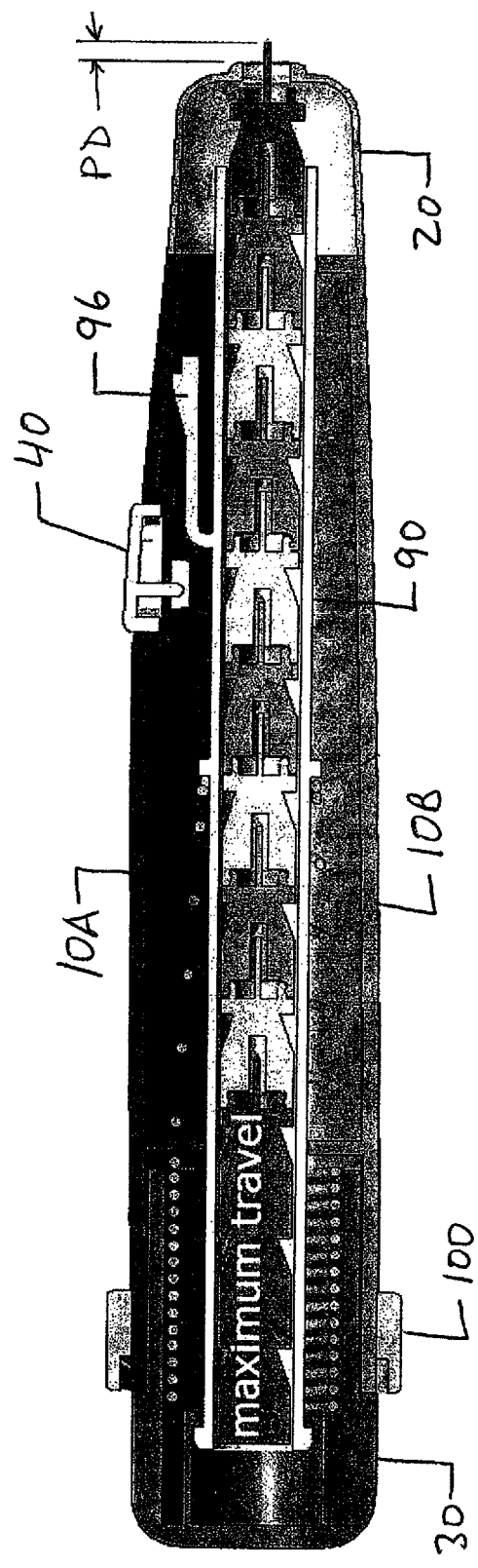
FIG. 8 shows a side cross-section view of FIG. 2. The device is shown in a triggered state and before the lancet holding member is automatically moved back to the position shown in FIG. 5.
Figure 11:
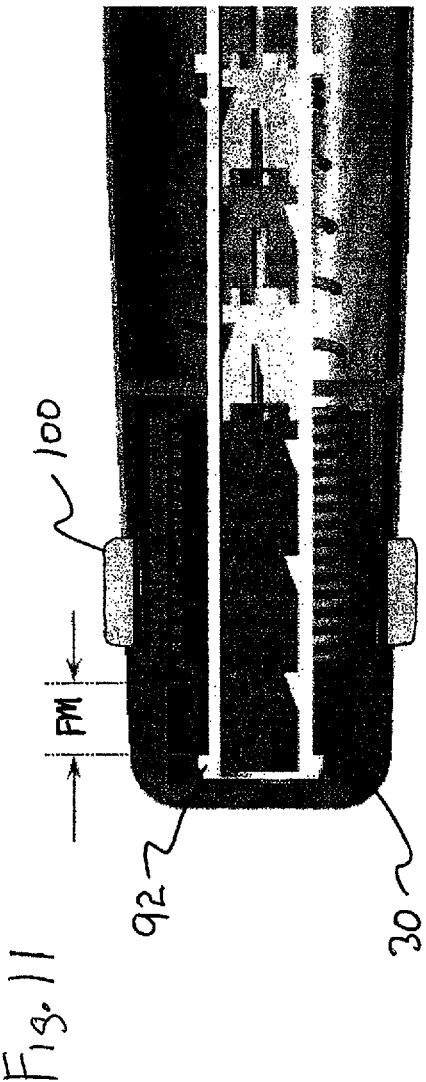
FIG. 11 shows an enlarged cross-section view of a rear portion of the lancet device and illustrates an amount of axial movement that the back cap can experience before the back cap causes rearward axial movement.
Figure 12:
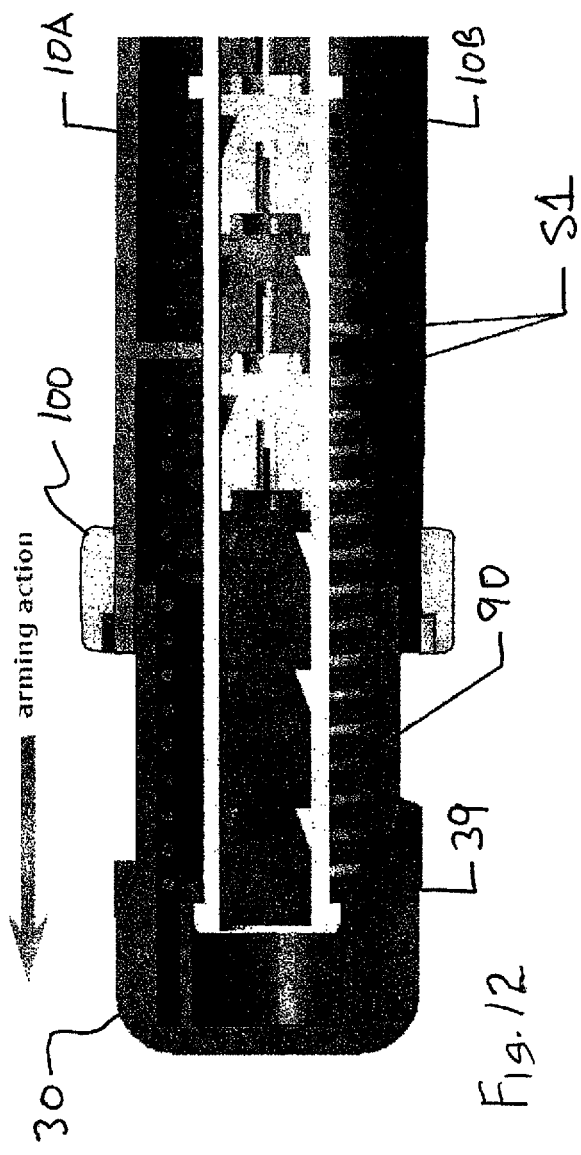
FIG. 12 shows another cross-section view of a rear portion of the lancet device. The back cap is shown moving the lancet holding member to an armed or trigger-set position.
Figure 17:
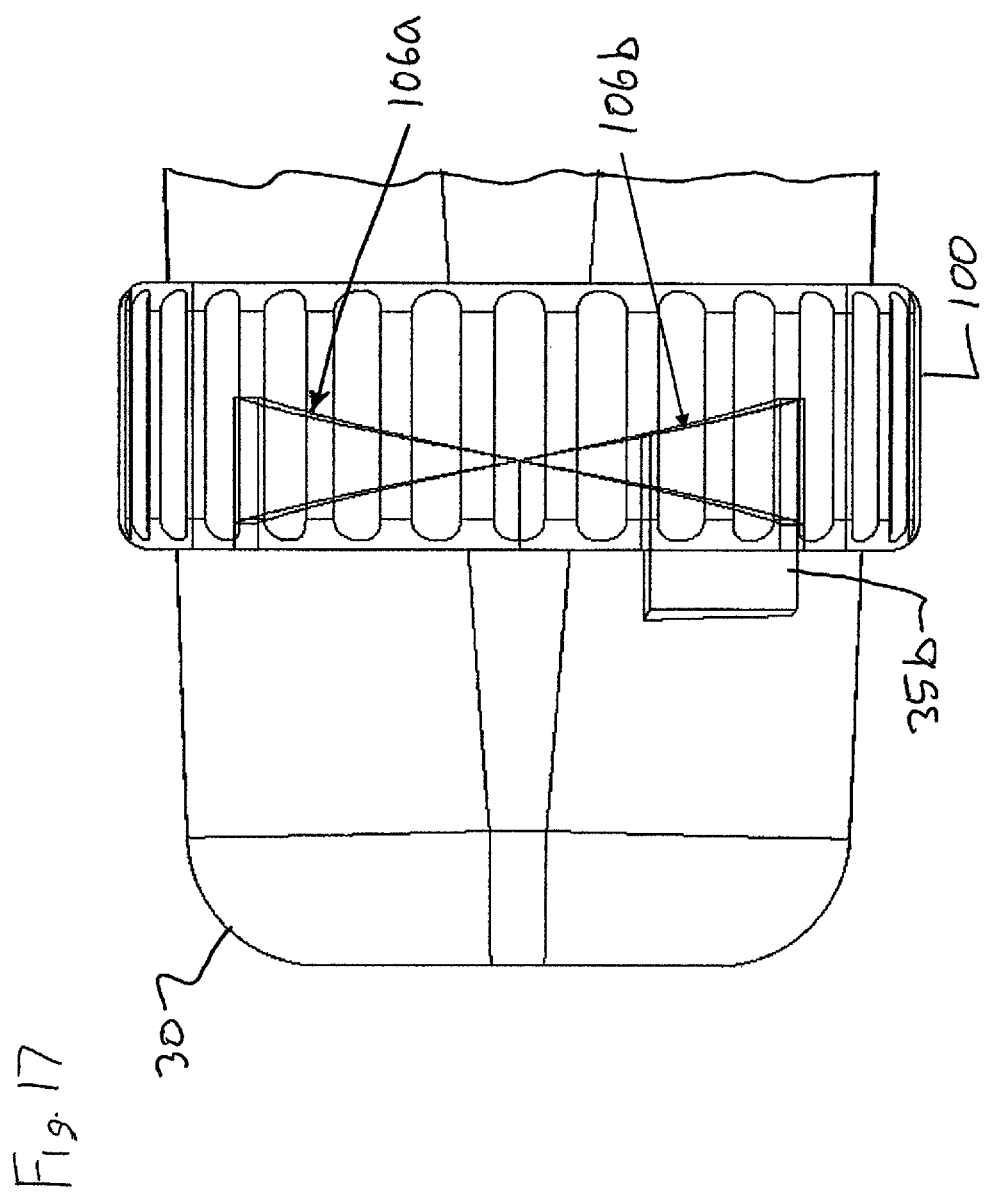
FIG. 17 shows a rear portion of the lancet device and illustrates the two tapered recesses (shown superimposed on each other) of the depth adjustment member or thumb wheel.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-53 show one non-limiting embodiment of a lancet device LD. The lancet device LD includes the following main components: a housing or body 10 which preferably comprises housing parts 10A and 10B, a front cap 20, a back cap 30, a trigger 40, a lancet advance button or member 50, a slide plate or member 60, a lancet engaging member 70, a locking member 80, a lancet holding member 90, a depth adjustment or thumb wheel member 100, and three springs S1, S2 and S3.

As can be seen in FIGS. 1-3, the lancet device LD can preferably have, by way of non-limiting example, an overall length OL which is approximately 133 mm and an overall width or diameter OD of approximately 27 mm. The lancet device LD can thus be held comfortably in a user's hand such that the user can rotate (both clockwise and counterclockwise) the depth adjustment thumb wheel 100 with the user's thumb and index finger, as will be described in detail later on, to set the depth of penetration prior to use. The user can also depress and slide forward the advance button 50 in order cause a forward advance of the lancet and simultaneously cause removal of the front cap 20, as will be described in detail later on. The user can also depress the trigger 40 with either the user's thumb of index finger. The only step which likely requires the user to use two hands, is the step of placing the lancet device LD is an armed or trigger-set position—which will be described in detail later on.

With reference to FIG. 4, the lancet device LD includes a removable front cap 20 which covers a front area of the lancet device LD that includes a front end of the lancet holding member 90, a first lancet FL, and a projecting portion 64 of the slide member 60. The first lancet FL is axially retained inside an elongated cylindrical opening 98 of the lancet holding member 90 by a deflectable tapered projection 97 which engages with a tapered portion TCS (see FIG. 53) of a lancet located directly behind the first lancet FL. Thus, when the lancet holding member 90 moves axially within housing 10, the lancet FL moves along therewith. With the exception of the last lancet LL (see FIGS. 50 and 51), all of the lancets are generally similarly and/or identically configured to the first lancet FL. To ensure that the multi-lancet unit (formed by the last lancet LL, the first lancet FL, and all of the lancets arranged therebetween) to move axially within the lancet holding member 90, the multi-lancet unit has an overall diameter LOD which is smaller than an internal diameter of the opening 98. By way of non-limiting example, the dimension LOD can be about 6.4 mm and the spacing or clearance (the difference between the two diameters divided by two) between these diameters can be between about 0.3 mm and about 1 mm. Although not shown, the front cap 20 can be removably secured to the housing 10 in a number of ways such as via a snap connection of the type disclosed in U.S. Pat. No. 5,908,434 to SCHRAGA and U.S. Pat. No. 6,530,937 to SCHRAGA. The disclosure of each of these documents is hereby expressly incorporated by reference in its entirety.

As can be seen in FIGS. 5-14, the lancet device LD functions as follows: In the position shown in FIGS. 5, 9, 11 and 13, the lancet device LD is shown in the static or initial position. This is the preferred position that the device would assume during shipping, storage, and after the device is triggered or fired. In this position, the front or triggering spring portion S1a of the spring S1 is in a relaxed or non-compressed or expanded position. The back or arming spring portion S1b of the spring S1 is also in a relaxed position, i.e., a non-expanded position, with the spring portion S1b applying a biasing force which forces the back cap 30 to a forward-most position. The advance button 50 and the trigger 40 are also in an initial position.

In the position shown in FIGS. 6, 10, 12 and 14, the lancet device LD is shown in the loading, arming or trigger-set position. This is the position which arms the lancet device and occurs when the user moves the back cap 30 rearwardly to cause the deflecting member 96 to become releasably locked to the retaining shoulder RS (see FIG. 25). In this position, the spring portion S1a is in a compressed state or position. Spring portion S1b is in an expanded state or position such that if the user were to release the back cap 30, the back cap 30 would automatically be moved to the position shown in FIGS. 5 and 7. The arming position shown in FIG. 6 can take place when the user grips the back cap 30 with one hand and the body 10 with the other hand and pulls the back cap 30 away from the body 10.

In the position shown in FIGS. 7 and 8, the lancet device LD is shown in the firing position. This is the position in which a user depresses the trigger 40 so as to cause the member 96 to deflect inwardly and release from the shoulder RS. This releases the energy stored in the spring S1a and causes the lancet holding member 90 to move forwardly, which automatically causes the forward-most or first lancet FL to project out of the front surface of the front cap 20 and cause a puncture in a user's skin. Of course, the position shown in FIGS. 7 and 8 merely shows a snap-shot of the lancet needle LN in the extended or puncturing position, i.e., defined by the puncturing depth PD. In actuality, the lancet needle LN would move from the position in FIG. 6 (fully retracted or trigger-set position) to that of FIGS. 7 and 8 (fully extended or puncturing position), and then finally to that of FIG. 5 (initial position) in a fraction of a second. In the firing position, the front spring portion S1a is in a substantially fully expanded position owing to the forward movement of the member 90 as caused by the rapid axial expansion of the spring S1a acting on the flange 94 of member 90. After the member 90 moves to a maximum forward position shown in FIG. 7, as determined by contact between shoulder 92 and shoulder 39, the spring S1a, which has substantially reached a maximum amount of allowable expansion, will contract axially back to an original position, which, in turn, places the lancet device LD back in the position shown in FIG. 5. At this point, the user has the option of activating the lancet advancing system LAS in order to cause removal of the front cap 20 and to allow for removal of the forward-most or used lancet FL so that the next or fresh lancet can assume the position as the first lancet FL as shown in FIG. 4.

With reference to FIGS. 9-12 and 15-17, it can be seen that the user can set a depth of penetration of the lancet device LD before the device is triggered or after the device is triggered. This can occur by the user rotating the thumb wheel 100 in either clockwise or counterclockwise directions. Such rotational movement determines the distance FM, i.e., the amount of free movement that the back cap 30 can experience in a rearward direction before it starts moving the lancet holding member 90 rearwardly. This distance FM also determines the amount of forward axial movement of the lancet holding member 90 as discussed above. This distance FM changes as a result of the rotational position of tapered recesses 105a and 105b of the thumb wheel 100 (see FIG. 33) relative to the projections 35a and 35b of the back cap 30 (see FIGS. 31 and 32), and more specifically as a result of the rotational position of tapered surfaces 106a and 106b of the thumb wheel 100 (see FIG. 33) relative to the tapered surfaces 36a and 36b of the back cap 30 (see FIGS. 31 and 32). The back cap 30 is kept from rotating substantially relative to the housing 10 by frictional or wedging engagement between the second end SE of the spring S1 (whose connecting portion CP is trapped or fixed to the housing by flanges 10A7 and 10B7) and the generally cylindrical annular groove formed between wall portions 38 and 34.

Figure 23:
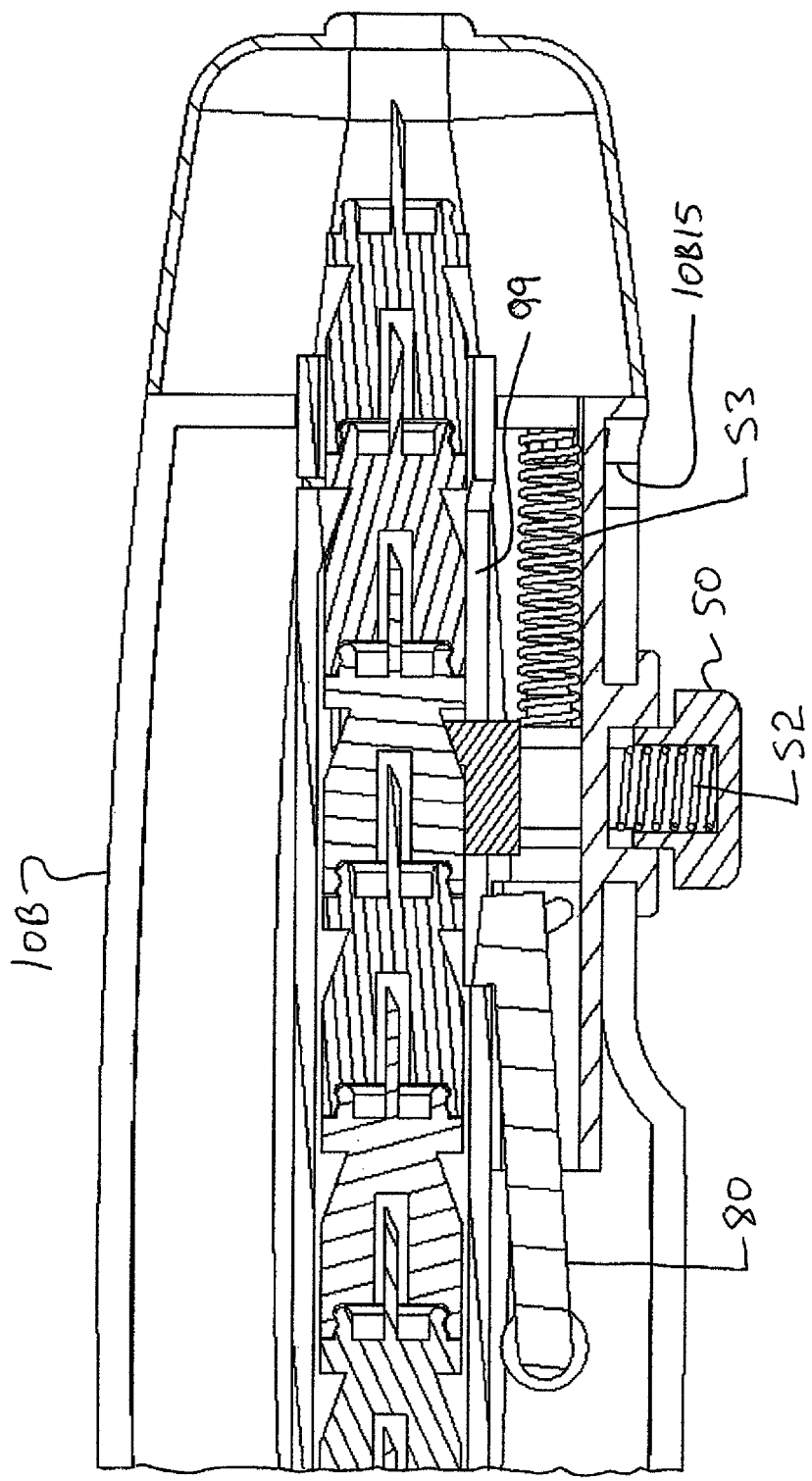
FIG. 23 shows the view of FIG. 21 after the system for advancing the multi-lancet unit is activated, i.e., the advance button is depressed and slid slightly forward.
Figure 24:
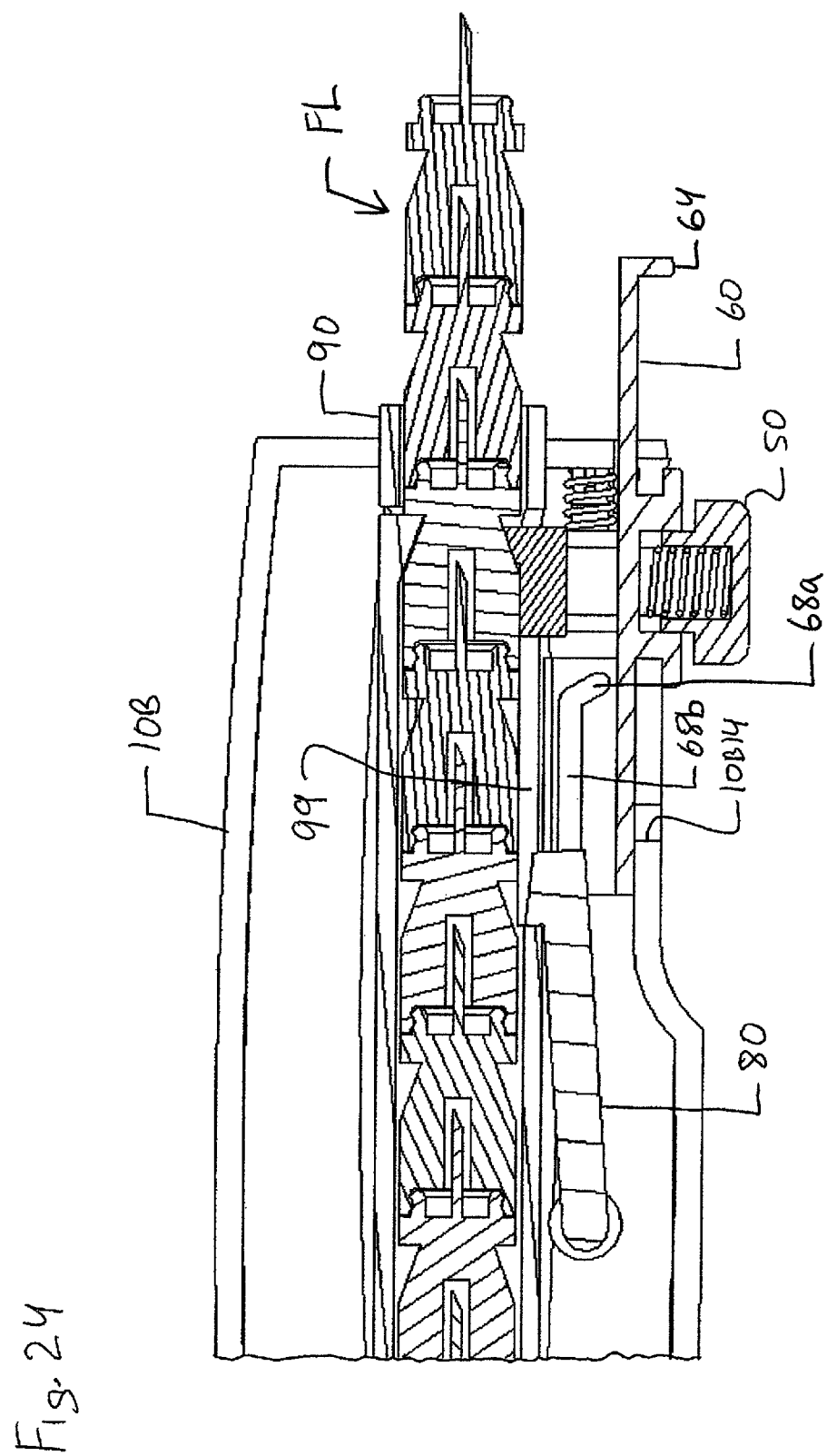
FIG. 24 shows the view of FIG. 23 after the system for advancing the multi-lancet unit is moved to a final activated position, i.e., the advance button is slid all of the way forward. This causes the front cap to be ejected and allows the user to break or snap-off the used lancet in order to expose a fresh or new lancet. The user can then release the advance button and replace the front cap in order to place the device back into an initial or intermediate position.

The details of the lancet advancing system LAS will now be described with reference to FIGS. 18-24. FIG. 18 illustrates the three steps utilized for advancing the multi-lancet unit within the lancet holding member 90. In step 1, the advance button 50 is depressed in the direction of the vertical arrow which causes the spring S2 to be compressed and causes the lancet engaging member 70 to pass through the slot 99 (see FIG. 39) and engage with the third lancet. In step 2, the advance button 70 is slid forward slightly against the biasing force of spring S3 which causes the slide plate 60 to slide in the forward direction. This initial forward movement of the slide plate 60 automatically causes the locking member 80 to pivot and engage with shoulder LS of the lancet holding member 90 in step 3. This pivoting movement of the locking member 80 occurs when the guide projection 88 is caused to move by engagement with the guide slot 68a. Continued forward sliding movement of the slide plate 60 causes the multi-lancet unit to move or advance forwards while the lancet holding member 90 is axially retained by the locking member 80. This forward movement of the slide plate 60 maintains the locking member 80 in the locking position because of continued engagement between the guide projection 88 and the guide slot 68b. FIGS. 18 and 21 illustrates the system LAS for advancing the multi-lancet unit installed in the lancet device LD in an initial position. FIG. 23 shows the view of FIG. 21 after the system LAS for advancing the multi-lancet unit is activated, i.e., the advance button 50 is depressed and slid slightly forward slightly. FIG. 24 shows the view of FIG. 23 after the system LAS for advancing the multi-lancet unit is moved to a final activated position, i.e., the advance button 50 is slid all of the way forward. This causes the front cap 20 to be ejected (by virtue of the projection 64 causing the edge 21 to disengage from the housing 10), moves the used lancet out past the front end of the lancet holding member 90 by a predetermined amount, and allows the user to break or snap-off (by separating the connection between portions RCP and RR) the used lancet FL in order to expose a fresh or new lancet. The user can then release the advance button 50 and re-install the front cap 20 in order to place the device LD back into an initial or intermediate position shown in FIG. 5.

The details of the parts utilized in the lancet device LD shown in FIGS. 1-3 will now be described with reference to FIGS. 25-53.

With reference to FIGS. 25 and 26, it can be seen that the left-side or upper housing part 10A includes a front end 10A1 which serves as a mounting area for the front cap 20 and a rear end 10A2. A front flange 10A3 is arranged in an area of the front end of the housing part 10A and includes a half or semi-circular opening 10A4 which (together with half-opening 10B4) is sized and configured to receive therein (allowing movement therethrough) a front end portion of the lancet holding member 90 (see FIGS. 39 and 40). The housing part 10A also has a main body portion 10A5 which is preferably ergonomically shaped. A projection 10A6 extends or projects from the body portion 10A5 and includes a mounting opening which is sized and configured to receive therein the mounting projection 86 of the pivotally mounted locking member 80 (see FIGS. 48 and 49). A rear flange 10A7 is arranged in an area of the rear end of the housing part 10A and includes a half-circular opening 10A8 which together with half-opening 10B8 is sized and configured to receive therein (allowing movement therethrough) a rear end portion of the lancet holding member 90 (see FIGS. 39 and 40). A rear generally half-cylindrical mounting surface 10A9 is arranged in an area of the rear end of the housing part 10A and together with half-cylindrical surface 10B9 is sized and configured to receive thereon (allowing rotational movement) the thumb wheel 100 (see FIGS. 33 and 34). A rear generally half or semi-cylindrical surface 10A16 is arranged in an area of the rear end of the housing part 10A and together with half-cylindrical surface 10B16 is sized and configured to receive therein (allowing sliding movement) the generally cylindrical surface 33 of the back cap 30 (see FIGS. 31 and 32). A trigger opening 10A10 is formed in the body portion 10A5 and is sized and configured to receive therein the projecting portions 43*a* and 43*b* of the trigger 40 (see FIGS. 35 and 36). Once inserted in the opening 10A10, the projecting portions 43*a* and 43*b* of the trigger 40 prevent removal of the trigger 40 from the housing part 10A, but allow the trigger 40 to move against the biasing force of two integrally formed deflecting members 10A11 which function as flat springs and bias the trigger 40 towards an extended or initial position. Each deflectable member 10A11 is deflected by contact with one of projections 44 of the trigger 40 when the trigger 40 is depressed. A retaining shoulder RS is formed in the body portion 10A5 and is configured to releasably engage and/or lock with a deflecting portion 96 of the lancet holding member 90 (see FIGS. 39 and 40). This releasable engagement is shown in FIG. 14. An indented section 10A12 is arranged in an area of the front end of the housing part 10A and together with indented section 10B12 forms an area for the user to activate the lancet advancing system LAS (see FIGS. 18-24). A half-slot 10A13 is arranged in an area of the front end of the housing part 10A and together with half-slot 10B13 forms a guide slot which guides the sliding movement of the slide plate 60 between an initial and final position (see FIGS. 23 and 24). The slide plate 60 contacts stop surface 10A14 in the initial position shown in FIG. 23 (as a result of the biasing force of the spring S3) and contacts stop surface 10A15 in the final position shown in FIG. 24 (as a result of the user causing compression of the spring S3). As is apparent from FIGS. 25 and 26, the housing part 10A can preferably be a one-piece member and is most preferably a one-piece synthetic resin member. Of course, the member 10A can also be an assembly of plural components provided it functions in a manner similar to that of the member shown in FIGS. 25 and 26.

With reference to FIGS. 27 and 28, it can be seen that the right-side or lower housing part 10B includes a front end 10B1 which serves as a mounting area for the front cap 20 and a rear end 10B2. A front flange 10B3 is arranged in an area of the front end of the housing part 10B and includes a half-circular opening 10B4 which (together with half-opening 10A4) is sized and configured to receive therein (allowing movement therethrough) a front end portion of the lancet holding member 90 (see FIGS. 39 and 40). The housing part 10B also has a main body portion 10B5 which is preferably ergonomically shaped. A projection 10B6 extends or projects from the body portion 10B5 and includes a mounting opening which is sized and configured to receive therein the mounting projection 87 of the pivotally mounted locking member 80 (see FIGS. 48 and 49). A rear flange 10B7 is arranged in an area of the rear end of the housing part 10B and includes a half-circular opening 10B8 which together with half-opening 10A8 is sized and configured to receive therein (allowing movement therethrough) a rear end portion of the lancet holding member 90 (see FIGS. 39 and 40). A rear generally half-cylindrical mounting surface 10B9 is arranged in an area of the rear end of the housing part 10B and together with half-cylindrical surface 10A9 is sized and configured to receive thereon (allowing rotational movement) the thumb wheel 100 (see FIGS. 33 and 34). A rear generally half-cylindrical surface 10B16 is arranged in an area of the rear end of the housing part 10B and together with half-cylindrical surface 10A16 is sized and configured to receive therein (allowing sliding movement) the generally cylindrical surface 33 of the back cap 30 (see FIGS. 31 and 32). A projection 10B16 projects from the flange 10B3 and functions as a mounting hub for a forward end of the spring S3 (see FIGS. 42 and 21). A recess or indentation 10B17 is formed in the flange 10B7 and is configured to receive therein and (together with flange 10A7) fixedly secure the connecting portion CP of the spring S1 (see FIG. 43). An indented section 10B12 is arranged in an area of the front end of the housing part 10B and together with indented section 10A12 forms an area for the user to activate the lancet advancing system LAS (see FIGS. 18-24). A half-slot 10B13 is arranged in an area of the front end of the housing part 10B and together with half-slot 10A13 forms a guide slot which guides the sliding movement of the slide plate 60 between an initial and final position (see FIGS. 23 and 24). The slide plate 60 contacts stop surface 10B14 in the initial position shown in FIG. 23 (as a result of the biasing force of the spring S3) and contacts stop surface 10B15 in the final position shown in FIG. 24 (as a result of the user causing compression of the spring S3). As is apparent from FIGS. 25 and 26, the housing part 10B can preferably be a one-piece member and is most preferably a one-piece synthetic resin member. Of course, the member 10B can also be an assembly of plural components provided it functions in a manner similar to that of the member shown in FIGS. 25 and 26.

With reference to FIGS. 29 and 30, it can be seen that the front cap 20 includes a skin contacting surface 25 which includes a lancet needle opening 24 sized and located to allow one of the lancet needles LN to pass or extend therethrough. The front cap 20 has an outer tapered generally rectangular surface 22, a rear end 21, and a generally planar front surface 23 Although not shown, the front cap 20 preferably include mechanisms, i.e., a recess and projection, to ensure that the front cap 20 is removably mounted to the front end of the housing 10. As is apparent from FIGS. 29 and 30, the front cap 20 can preferably be a one-piece member and is most preferably a one-piece synthetic resin member. Of course, the front cap 20 can also be an assembly of plural components provided it functions in a manner similar to that of the member shown in FIGS. 29 and 30.

With reference to FIGS. 31 and 32, it can be seen that the back cap 30 includes a front end 31 and a generally cylindrical through opening 32 which is sized to allow the rear end of the lancet holding member 90 to move therein (see e.g., FIGS. 9 and 10). An enlarged rear portion 34 sized and configured to allow the user to grip the back cap 30. The back cap 30 also includes two oppositely arranged projections 35a and 35b which are sized to extend into two spacings formed by the two grooves 105a and 105b and the cylindrical surface formed by surfaces 10A9 and 10B9. These projections 35a and 35b have tapered front surfaces 36a and 36b which are adapted to slidably engage with tapered surfaces 106a and 106b of the semi-circumferential grooves 105a and 105b. The depth of penetration PD (see FIG. 8) is adjusted or predetermined by the relative rotational position of the tapered front surfaces 36a and 36b and groove surfaces 106a and 106b. A shoulder 37 is configured to abut the ends 10A2 and 10B2 of the housing 10 when the back cap 30 is in an initial or resting position (see e.g., FIG. 5). As is shown in FIG. 9, the back cap 30 also includes a generally cylindrical inner sleeve portion 38 which has an inwardly facing tapered circumferential shoulder 39 which is configured to contact the outward facing circumferential projection 92. Contact between projections 39 and 92 takes place when the back cap 30 is moved to the arming position shown in FIGS. 10 and 12, as well as when the lancet holding member 90 moves to the fully extended or puncturing position shown in FIGS. 7 and 8. The annular space formed by the inner circumferential surface of portion 34 and the outer cylindrical surface of portion 38 is sized to receive therein and securely wedge or trap the second end SE of the spring S1. This allows the spring portion S1b to bias the back cap 30 towards the position shown in FIG. 5 and automatically moves the back cap 30 back to the position shown in FIG. 5 when the user releases the back cap 30 from the position shown in FIG. 6. As is apparent from FIGS. 31 and 32, the back cap 30 can preferably be a one-piece member and is most preferably a one-piece synthetic resin member. Of course, the back cap 30 can also be an assembly of plural components provided it functions in a manner similar to that of the member shown in FIGS. 31 and 32.

With reference to FIGS. 33 and 34, it can be seen that the depth adjustment member or thumb wheel 100 includes an annular rear end 101 which is configured to slidably engage with portions of shoulder 37 and an annular front end 102 which is configured to slidably engage with the shoulder formed by annular shoulder portions 10A18 and 10B18. A generally cylindrical through opening 103 is sized to rotatably engaged with and mount to cylindrical surfaces 10A9 and 10B9. The thumb wheel 100 also includes an outer surface 104 having ribs and indentations which allow a user to easily grip the thumb wheel 100 and rotate it relative to the housing 10 in each of a clockwise and counterclockwise directions. Other types of friction surfaces can also be utilized. The thumb wheel 100 also includes two oppositely arranged semi-circumferential grooves 105a and 105b which open to the rear end 101 and are sized and configured to receive therein the two projections 35a and 35b and the cylindrical surface formed by surfaces 10A9 and 10B9. Tapered surfaces 106a and 106b of the semi-circumferential grooves 105a and 105b are configured to slidably engage with tapered front surfaces 36a and 36b. The depth of penetration PD (see FIG. 8) is adjusted or predetermined by the rotational position of the thumb wheel 100 relative to the housing 10 and more specifically by the rotational position of the groove surfaces 106a and 106b relative to the tapered front surfaces 36a and 36b. Maximum depth of penetration PD (see FIG. 8) results when the two projections 35a and 35b contact stop surfaces 107a and 108a and whereas minimum depth of penetration PD results when the two projections 35a and 35b contact stop surfaces 107b and 108b. Although not shown, the lancet device LD can utilize a system for indicating to the user the position of depth adjustment, i.e., thumb wheel 100, so that the user can determine whether to change the depth of penetration. This system can, by way of non-limiting example, take the form of indicia, e.g., numbers or letters, arranged on the housing 10 in an area of the thumb wheel 100. An indicator, e.g., an arrow head, can be arranged on the thumb wheel 100. As is apparent from FIGS. 33 and 34, the thumb wheel 100 can preferably be a one-piece member and is most preferably a one-piece synthetic resin member. Of course, the thumb wheel 100 can also be an assembly of plural components provided it functions in a manner similar to that of the member shown in FIGS. 33 and 34.

Figure 36:
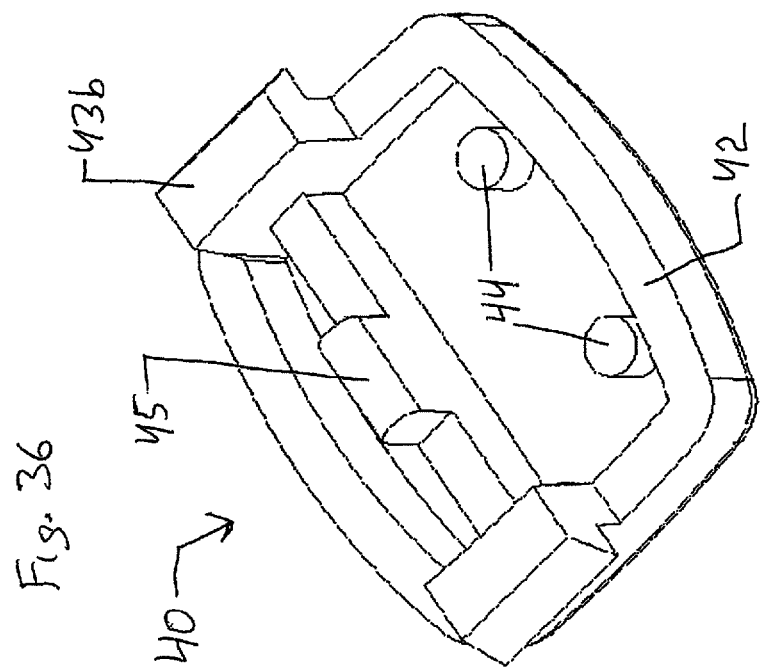
FIG. 36 shows a perspective inside view of the trigger shown in FIG. 35.
Figure 35:
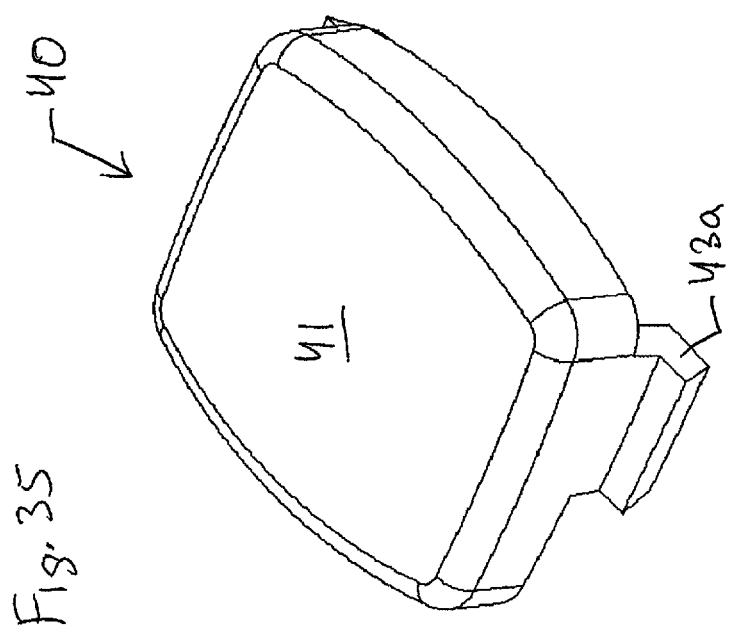
FIG. 35 shows a perspective top side view of the trigger used in the lancet device shown in FIGS. 1-3.

With reference to FIGS. 35 and 36, it can be seen that the trigger 40 includes a generally rectangular top surface 41 which is configured to be contacted by a user finger. The trigger 40 also includes two oppositely arranged projections 43a and 43b which are configured to snap into the opening 10A10 and prevent removal of the trigger 40 once installed on the body portion 10A. Two generally circular projections 44 are spaced apart and configured to contact free end portions of the two deflectable members 10A11. A generally rectangular projection 45 is configured to contact the deflectable member 96 and cause the shoulder of the deflectable member 96 (see FIGS. 39 and 40) to disengage from the retaining shoulder RS when the lancet device LD is in a trigger-set position (see e.g., FIG. 14) and the trigger 40 is depressed. As is apparent from FIGS. 35 and 36, the trigger 40 can preferably be a one-piece member and is most preferably a one-piece synthetic resin member. Of course, the trigger 40 can also be an assembly of plural components provided it functions in a manner similar to that of the member shown in FIGS. 35 and 36.

Figure 38:
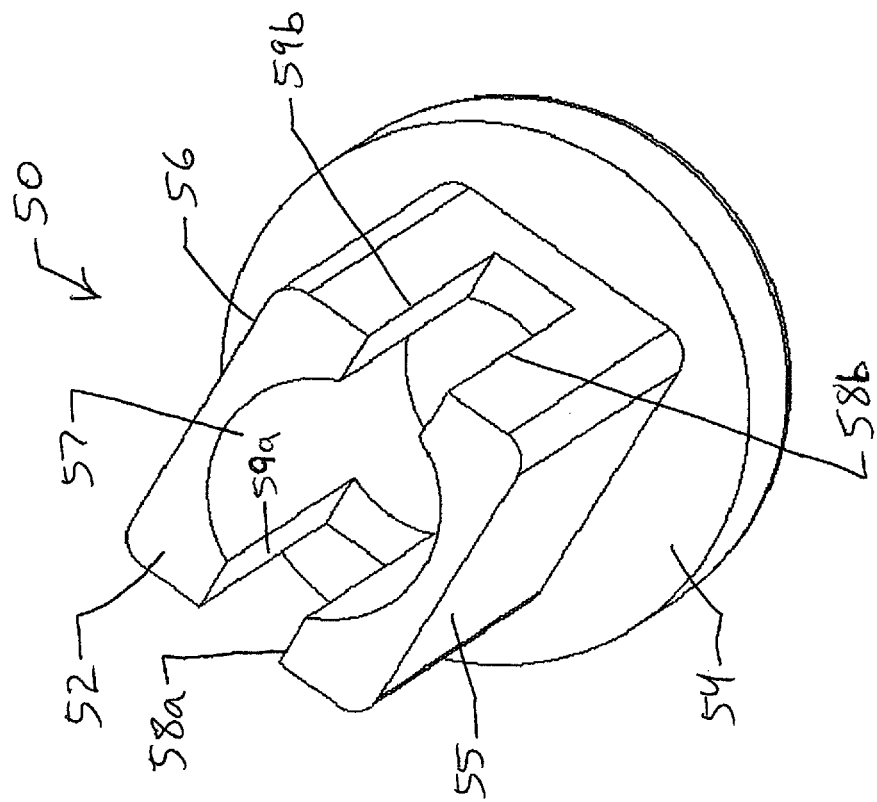
FIG. 38 shows a perspective inside view of the advance button shown in FIG. 37.
Figure 37:
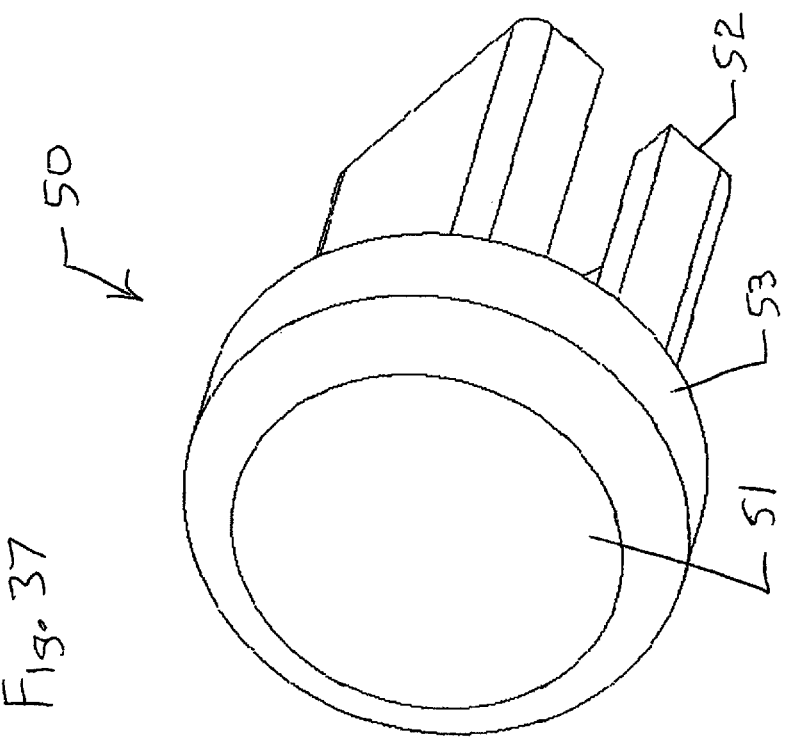
FIG. 37 shows a perspective top side view of the advance button used in the lancet device shown in FIGS. 1-3.

With reference to FIGS. 37 and 38, it can be seen that the advance member or button 50 includes a generally circular top surface 51 which is configured to be contacted by a user finger. A generally rectangular bottom end 52 is arranged at a bottom of a generally rectangular projection which slidably engages with rectangular opening 66 (see FIG. 44) and has two oppositely arranged planar surfaces 55 and 56. A through slot is formed by surfaces 50a-58b and 59a-59b. These surfaces 50a-58b and 59a-59b are configured to frictionally and/or securely engaged with the oppositely arranged projections 77 and 78 of the lancet engaging member 70 (see FIGS. 46 and 47). This connection results in the surfaces 75 and 76 being retained in the slot formed by surfaces 50a-58b and 59a-59b and ensures that the member 70 is secured to the button 50 (so as to move therewith)—with the plate member 60 interposed therebetween. The member 50 also includes a side surface 53, a bottom surface 54, and a generally cylindrical opening 57. The opening 57 is sized and configured to receive therein the advance button spring S2 (see 41 and FIGS. 18-20). The spring S2 is compressed when the button 50 is moved towards the plate 60 (see FIG. 23) and more specifically when surface 54 in the opening 57 moves toward the plate 60. The two projections formed by surfaces 58a, 58b and 55 and by surfaces 59a, 59b and 56 are each sized to pass through the generally rectangular through openings 66a and 66b of the plate member 60. When the button 50 is depressed, the spring S2 is compressed and the lancet engaging member 70 (secured to the member 50) passes into the slot 99 and engages with one of the lancets (see FIG. 23). As is apparent from FIGS. 37 and 38, the advance button 50 can preferably be a one-piece member and is most preferably a one-piece synthetic resin member. Of course, the button 50 can also be an assembly of plural components provided it functions in a manner similar to that of the member shown in FIGS. 37 and 38.

With reference to FIGS. 39 and 40, it can be seen that the lancet holding member 90 includes an annular front end 91 and an annular rear end which includes a generally circular circumferential shoulder 92 configured to contact shoulder 39 of the back cap 30. The member 90 has a generally cylindrical body portion 93 sized to slidably engaged with the circular openings formed semi-circular indentations 10A4 and 10B4 and 10A8 and 10B8. The member 90 also includes a circumferential projection 94 and a retaining projection 95 which together are configured to axially secure the first end FE of the spring S1 to the member 90. Because the spring portion S1a has a connecting portion CP which is fixed to the housing 10 and a first end FE fixed to the holding member 90 via projections 94 and 95, the spring portion S1a is capable of causing movement of the lancet holding member 90 to the extended or puncturing position and a retraction thereof back to the initial position shown in FIG. 5. The member 90 also includes a generally cylindrical through opening 98 which is sized and configured to receive a multi-lancet unit which can be made up of a last lancet LL (see FIGS. 50 and 51) and plural other lancets, e.g., nine other lancets which terminate in a first lancet FL. The multi-lancet unit can be made up of any desired number of lancets provided the last lancet LL is utilized. Moreover, the multi-lancet unit can be installed into the lancet holding member 90 via the opening 32 formed in the back cap 30., i.e., by sliding it into the lancet device LD from a rear end thereof. Once all of the lancets are used up (i.e., the last lancet LL is used for puncturing), the lancet device LD can either be disposed of or the user can slide a new multi-lancet unit into the lancet holding member 90 from the rear side of the lancet device LD and place in into the position shown in FIG. 5. This insertion causes the last lancet LL to be ejected out of the front end 91. To protect the needle LN of the first lancet on installation into the lancet device LD, the lancet needle LN can have a removable protection mechanism of the type disclosed in U.S. Pat. No. 5,464,418 to SCHRAGA, the disclosure of which is hereby expressly incorporated by reference in its entirety (e.g., member 62 of U.S. Pat. No. 5,464,418). The member 90 also includes a deflectable locking projection 97 which has an inward facing tapered projection portion sized and configured to engage with the tapered surface TCS of each lancet. The shape of the taped inner section of projection 97 is such that it only permits forward movement of the multi-lancet unit. This engagement (see e.g., FIG. 4) ensures that the multi-lancet unit is axially within the member 90 (and moves therewith) until the user causes the multi-lancet unit to move within the member 90 via the lancet advancing system LAS. In this regard, the member 90 includes an elongated slot 99 which is sized to receive therein the engaging portion 73 of the lancet engaging member 70. The slot 99 allows the portion 73 to engage with the tapered surface TCS of each lancet. Finally, the member 90 includes a deflectable projecting portion 96 which has a shoulder that can be retained or locked to the retaining shoulder RS (see FIGS. 25 and 14) when the lancet device LD is in a trigger-set or armed position and which can be released from such engagement when the user depresses the trigger 40. As is apparent from FIGS. 39 and 40, the member 90 can preferably be a one-piece member and is most preferably a one-piece synthetic resin member. Of course, the member 90 can also be an assembly of plural components provided it functions in a manner similar to that of the member shown in FIGS. 39 and 40.

Figure 43:
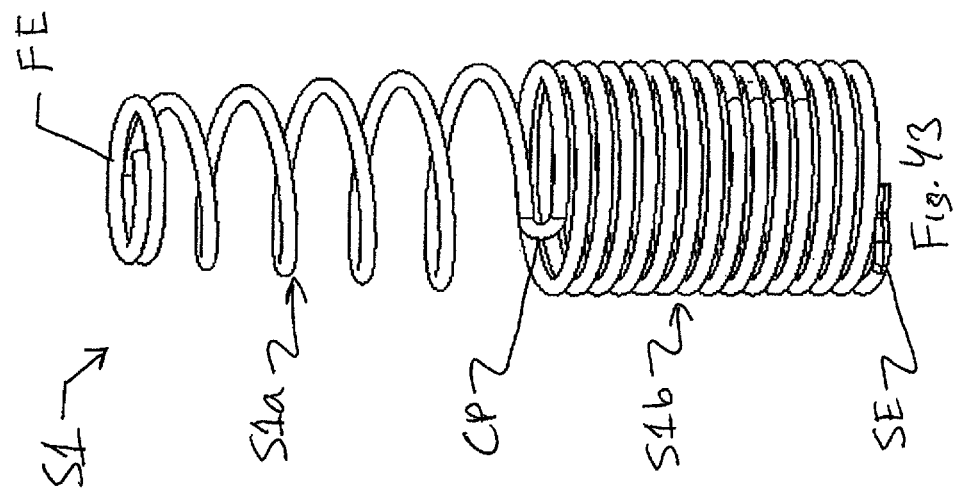
FIG. 43 shows a perspective side view of the dual-purposes spring used on the lancet device of FIGS. 1-3. The spring has a front portion which causes the lancet holding member to move to the puncturing position and automatically retracts the lancet holding member after doing so. The spring also has a rear portion which causes the back cap to move to an initial position after the user moves the back to the arming position and release the back cap.
Figure 42:
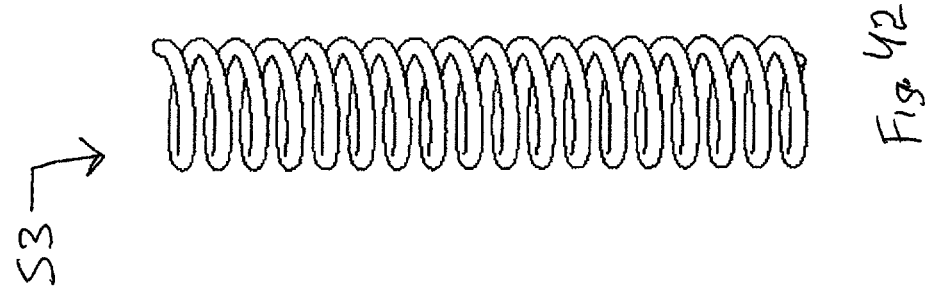
FIG. 42 shows a perspective side view of the slide return spring used on the lancet device of FIGS. 1-3.
Figure 41:
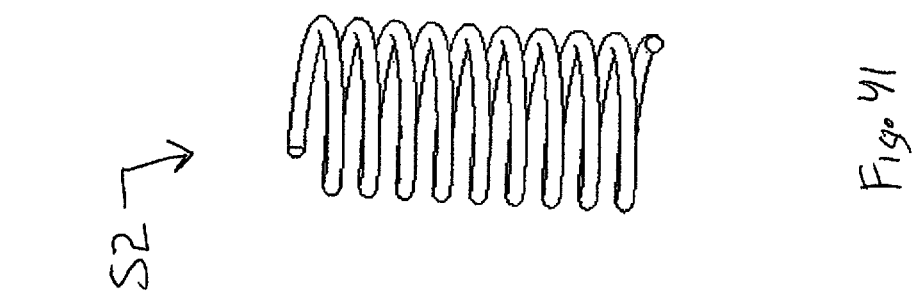
FIG. 41 shows a perspective side view of the advance button spring used on the lancet device of FIGS. 1-3.

With reference to FIGS. 41-43, it can be seen that the main spring S1, the advance button spring S2 and the slide plate return spring S3 can have the form of helical wire compression springs. Each spring S1-S3 is preferably be a one-piece member and is most preferably a one-piece spring metal member. Of course, the springs can also be made of any material provided they function in a manner similar to that of the members shown in FIGS. 41-43. The spring S1 can also take the form of two springs each having the characteristics of portions S1a and S1b.

With reference to FIGS. 44 and 45, it can be seen that the slide plate member 60 includes a rear end 62 and a forward end 61 having an upstanding projection 64 configured to contact the edge 21 of the front cap 20 and causes removal of the front cap 20 when the lancet advancing system LAS is activated (see FIG. 24). A generally rectangular surface 63 is configured to slidably engage with a generally planar surface form by the inside surfaces of portions 10A12 and 10B12. A projecting portion extends from one side of the plate portion 63 and includes a generally rectangular surface 65 and a generally rectangular opening 66 which is sized to slidably receive therein a bottom portion of the advance button 50. An opposite facing surface to surface 65 is configured to slidably engage with a generally planar surface form by the outside surfaces of portions 10A12 and 10B12. The opposite side of the plate portion 63 includes a generally rectangular plate projection 67 which includes a cam or guide slot 68 which is sized and configured to receive therein a guide projection 88 of the locking member 80 (see FIGS. 48 and 49). The guide slot 68 has a beginning portion 68a which causes an almost immediate pivoting of the member 80 when the button 50 is depressed and the slide plate 60 is caused to move forward slightly (see FIG. 23) and a secondary portion 68b which maintains the pivoting position of member 80 and allows the plate 60 to move forwardly. The member 60 also includes two generally rectangular openings 66a and 66b which are each sized to allow passage therethrough of the two projecting portions of the advance button 50. The two projections formed by surfaces 58a, 58b and 55 and by surfaces 59a, 59b and 56 are each sized to pass through and slidably engage with the generally rectangular through openings 66a and 66b of the plate member 60. Finally, the opposite side of the plate portion 63 includes another generally rectangular projection which includes a generally cylindrical projection 69 sized and configured to extend into one of the ends of the spring S3 (see FIG. 22). As is apparent from FIGS. 44 and 45, the slide plate 60 can preferably be a one-piece member and is most preferably a one-piece synthetic resin member. Of course, the member 60 can also be an assembly of plural components provided it functions in a manner similar to that of the member shown in FIGS. 44 and 45.

With reference to FIGS. 46 and 47, it can be seen that the lancet engaging member 70 includes a generally rectangular bottom surface 71 and a tapered engaging section 73 which is configured to engage with surface TCS of the lancets. A generally circular section 74 is configured to into the opening 57 of the advance button 50. Two oppositely arranged surfaces 75 and 76 include tapered securing projections 77 and 78 and are configured to engage with the slot formed by surfaces 50a-58b and 59a-59b. These surfaces 50a-58b and 59a-59b are configured to frictionally and/or securely engaged with the oppositely arranged projections 77 and 78 of the lancet engaging member 70. This connection results in the surfaces 75 and 76 being retained in the slot formed by surfaces 50a-58b and 59a-59b and ensures that the member 70 is secured to the button 50 (so as to move therewith)—with the plate member 60 interposed therebetween. As is apparent from FIGS. 46 and 47, the lancet engaging member 70 can preferably be a one-piece member and is most preferably a one-piece synthetic resin member. Of course, the member 70 can also be an assembly of plural components provided it functions in a manner similar to that of the member shown in FIGS. 46 and 47.

Figure 49:
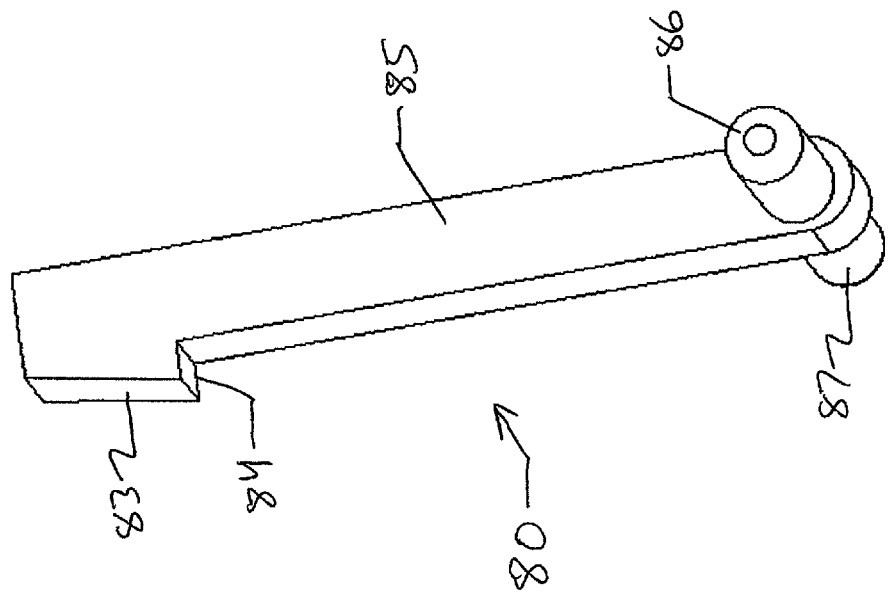
FIG. 49 shows a perspective right-side view of the locking member shown in FIG. 48.
Figure 48:
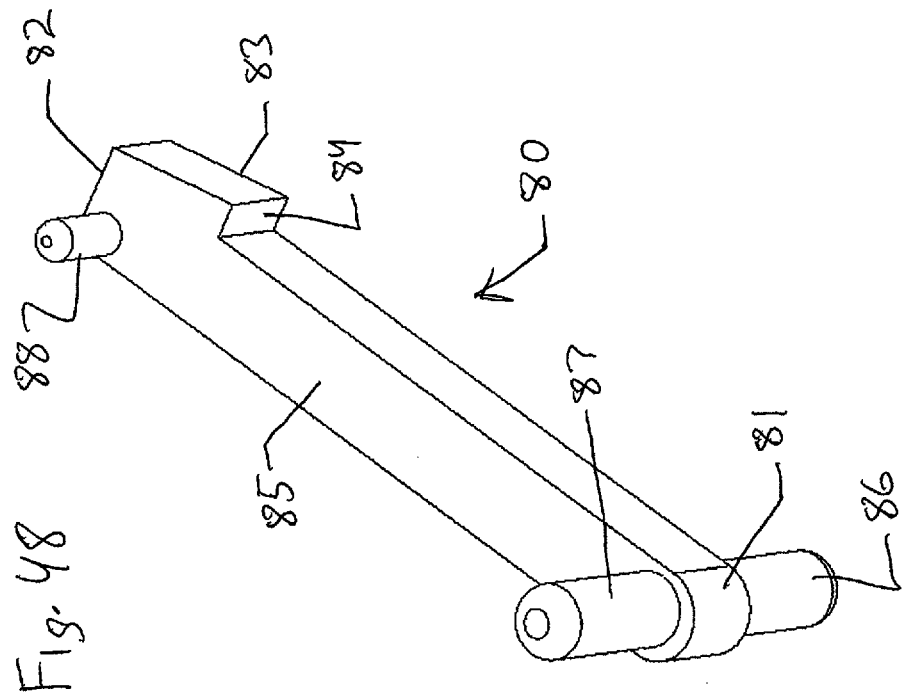
FIG. 48 shows a perspective left-side view of the locking member used in the lancet device shown in FIGS. 1-3.

With reference to FIGS. 48 and 49, it can be seen that the locking member 80 includes a generally rectangular section 85, a tapered engaging section 83 having a retaining shoulder 84 which is configured to engage with shoulder LS of the lancet holding member 90. A generally cylindrical projection 88 is configured to engage with the slot 68 in the slide plate 60. Two oppositely arranged generally cylindrical projections 86 and 87 are sized and configured to extend into the openings formed in projections 10A6 and 10B6 and form the pivot mounting for the locking member 80. As is apparent from FIGS. 48 and 49, the locking member 80 can preferably be a one-piece member and is most preferably a one-piece synthetic resin member. Of course, the member 80 can also be an assembly of plural components provided it functions in a manner similar to that of the member shown in FIGS. 48 and 49.

Figure 51:
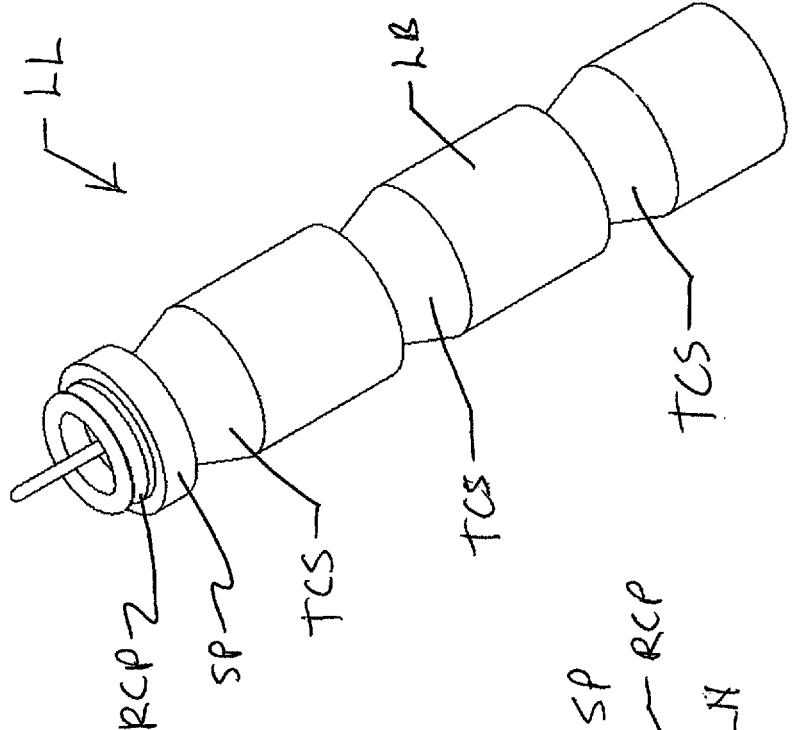
FIG. 51 shows a perspective right-side view of the last lancet shown in FIG. 50.
Figure 50:
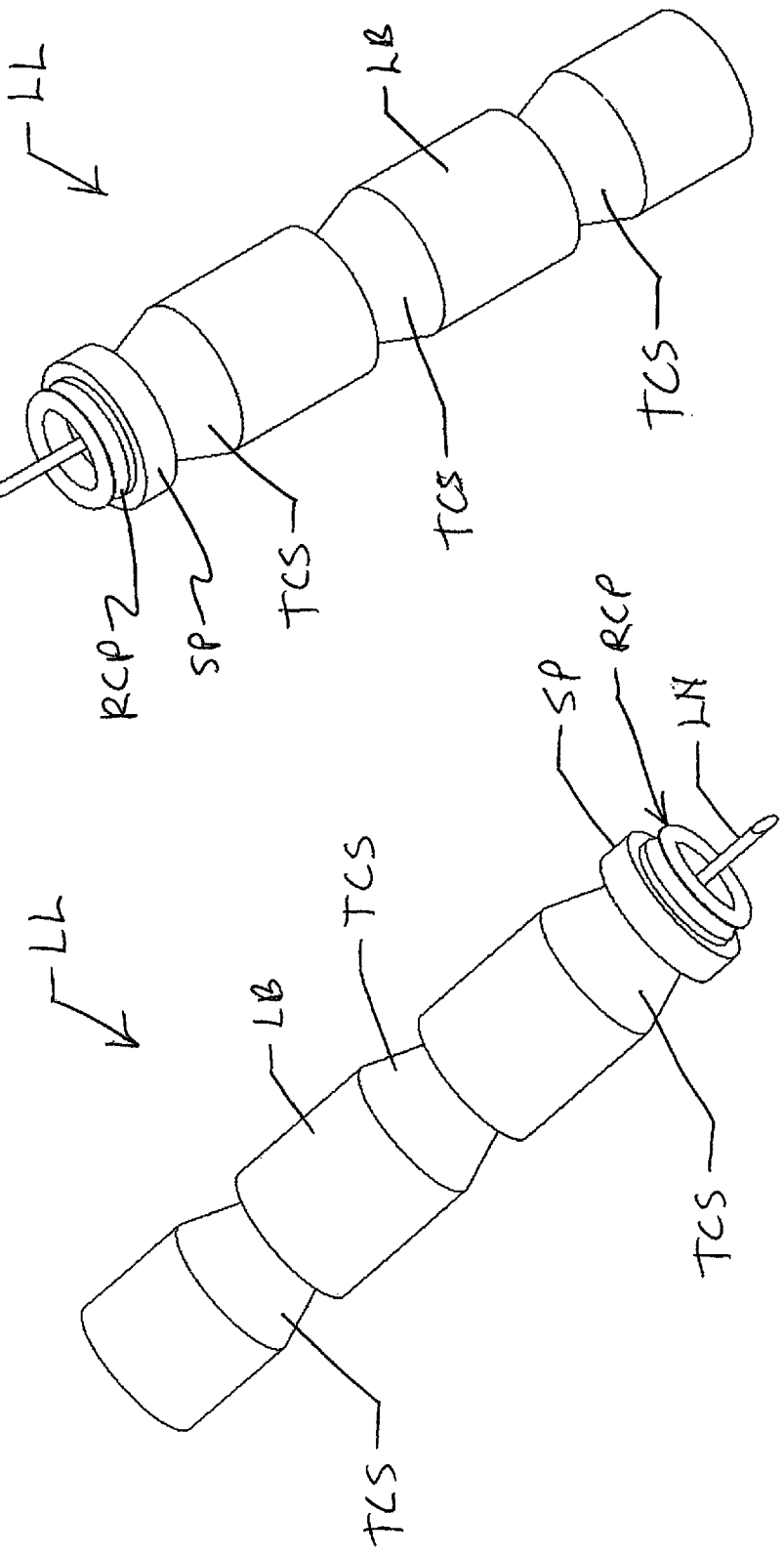
FIG. 50 shows a perspective left-side view of the last lancet of the multi-lancet unit used in the lancet device shown in FIGS. 1-3.

With reference to FIGS. 50 and 51, it can be seen that the last lancet LL includes a lancet needle LN, a lancet body LB having three tapered sections TCS, a support shoulder SP, and a releasable connecting portion RCP. The section RCP can be configured to snap-into a recess RR formed in a lancet arranged in front of the last lancet LL and has a outwardly cured front section followed by an inwardly curved section. This allows the connection to be separated by bending over the lancet in front of the last lancet LL. The lancet needle LN can be of any size typically used for lancet needles and preferably has a sharp free end which is configured to puncture a user's skin while causing minimal pain. The front surface is of the shoulder SP can be generally circular and is configured to be contacted by or abut the rear end RE of the lancet in front thereof. The main body portion LB is generally cylindrical and is sized and configured to freely slide within opening 98 of the member 90. As is apparent from FIGS. 50 and 51, the last lancet LL can preferably be a one-piece member (with the exception of the lancet needle LN) and is most preferably a one-piece synthetic resin member. Of course, the lancet LL can also be an assembly of plural components provided it functions in a manner similar to that of the member shown in FIGS. 50 and 51.

With reference to FIGS. 52 and 53, it can be seen that the first or front lancet FL (as well as all of the other lancets except for the last lancet LL) includes a lancet needle LN, a lancet body LB having a tapered section TCS, a support shoulder SP, and a releasable connecting portion RCP. The section RCP can be configured to snap-into a recess RR formed in a lancet arranged in front thereof and has a outwardly cured front section followed by an inwardly curved section. This allows the connection to be separated by bending over the lancet in front. The lancet needle LN can be of any size typically used for lancet needles and preferably has a sharp free end which is configured to puncture a user's skin while causing minimal pain. The front surface is of the shoulder SP can be generally circular and is configured to be contacted by or abut the rear end RE of the lancet in front thereof. The main body portion LB is generally cylindrical and is sized and configured to freely slide within opening 98 of the member 90. As is apparent from FIGS. 52 and 53, the first lancet FL (and other lancets except for the last lancet LL) can preferably be a one-piece member (with the exception of the lancet needle LN) and is most preferably a one-piece synthetic resin member. Of course, the lancet FL can also be an assembly of plural components provided it functions in a manner similar to that of the member shown in FIGS. 52 and 53.

One or more of the parts of the lancet device LD such as, e.g., the housing 10 and front cap 20 can preferably made transparent and/or translucent so that a user will clearly be able to see internal components. The device can also utilize one or more features or modifications disclosed in US 2006/0173478 to SCHRARA, the disclosure of which is hereby expressly incorporated by reference in its entirety.

It is also possible to utilize an indicator system to inform the user which lancet needle has already been used and/or how many new or unused lancets remain in the multi-lancet unit. Non-limiting examples of such a system include making the last lancet LL of a different color than the lancet sin front thereof so that the user will know that the device can thereafter be disposed of or requires a new multi-lancet unit. All the parts of the lancet device LD, with the exception of the springs and needles (which can respectively be made of spring steel and stainless steel), may be made from plastic materials and can be formed using conventional injection molding techniques or other known manufacturing methods. Bay way of non-limiting example, all or most of the parts such as the housing, trigger, front and back caps, thumb wheel, advance button, slide plate, lancet engaging member, locking member can be made of ABS plastic with the exception of the springs (which can be stainless steel) and the lancet holding member which can be made of polyoxymethylene (Delrin plastic). However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A lancet device comprising:
    a housing;
    a trigger having a portion extending outside the housing so as to be contacted by a user;
    a front cover having a skin engaging surface and an opening allowing a needle of a lancet to pass therethrough during skin puncturing;
    a cocking system configured to place the lancet device in a trigger-set or armed position;
    the cocking system comprising a cocking member arranged in an area of a rear end of the housing;
    a multi-lancet unit comprising a plurality of lancets arranged one in front of the other and positioned in the housing;
    each lancet comprising a front end, a needle which extends from the front end, and a rear end;
    a lancet holding member receiving therein the multi-lancet unit and being movable within the housing; and
    a lock member that is movable to a locking position that prevents axial movement of the lancet holding member,
    wherein, when the lock member is not in the locking position, the holding member is capable of moving between an initial position, a trigger-set position, and a puncturing position, wherein the front end of at least one of the plurality lancets is removably connected to the rear end of another of the plurality of lancets.

2. The lancet device of claim 1, wherein the plurality of lancets comprises two lancets.

3. The lancet device of claim 1, wherein the plurality of lancets comprises at least three lancets.

4. The lancet device of claim 1, wherein the plurality of lancets is between five lancets and twenty lancets.

5. The lancet device of claim 1, wherein the plurality of lancets is between eight lancets and twelve lancets.

6. The lancet device of claim 1, wherein each of the plurality of lancets comprises a generally cylindrical portion.

7. The lancet device of claim 1, wherein each of the plurality of lancets comprises a generally circular cross-section when viewed perpendicular to a center axis of the plurality of lancets.

8. The lancet device of claim 1, wherein at least one of the plurality of lancets comprises a locking mechanism.

9. The lancet device of claim 8, wherein the locking mechanism comprises at least one of a circumferential locking recess and a tapered recess.

10. The lancet device of claim 1, wherein each of the plurality of lancets comprises a locking recess.

11. The lancet device of claim 1, further comprising a depth adjustment system.

12. A method of puncturing a surface of skin using the lancet device of claim 11, the method comprising:
arranging the lancet device adjacent against a user's skin; and
triggering the lancet device so that one of the plurality of lancets is caused to penetrate the user's skin.

13. The lancet device of claim 1, further comprising:
a depth adjustment system; and
the lancet holding member comprising:
an opening arranged behind a front end of the lancet holding member;
an integrally formed deflecting member; and
a longitudinal length that is greater than a longitudinal length of the housing.

14. The lancet device of claim 1, further comprising:
a rotatably mounted depth adjustment element.

15. The lancet device of claim 1, further comprising at least one of:
a system for removing or ejecting a lancet of the plurality of lancets; and
a system for advancing or positioning an unused lancet into a position previously held by a used lancet that has been removed.

16. The lancet device of claim 1, further comprising a manually activated system for removing or ejecting a used lancet of the multi-lancet unit.

17. The lancet device of claim 1, further comprising a system for removing or ejecting a used lancet of the multi-lancet unit and for causing removal of the front cover.

18. A method of puncturing a surface of skin using the lancet device of claim 17, the method comprising:
arranging the lancet device adjacent against a user's skin; and
triggering the lancet device so that one of the plurality of lancets is caused to penetrate the user's skin.

19. A method of puncturing a surface of skin using the lancet device of claim 1, the method comprising:
arranging the lancet device adjacent against a user's skin; and
triggering the lancet device so that one of the plurality of lancets is caused to penetrate the user's skin.

20. A lancet device comprising:
a housing;
a front cap having a skin engaging surface and a lancet opening allowing for passage therethrough of a lancet needle during skin puncturing;
a trigger;
a depth adjustment system arranged in an area of a rear end of the housing;
a plurality of lancets arranged one in front of the other and positioned in the housing;
each lancet comprising a front end, a needle which extends from the front end, and a rear end;
an advance button movable between a first position and a position causing each of:
ejection of one of the lancets; and
removal of the front cap,
wherein the front end of at least one of the plurality lancets is removably connected to the rear end of another of the plurality of lancets.

21. The lancet device of claim 20, wherein the plurality of lancets comprise at least three lancets.

22. The lancet device of claim 20, wherein the plurality of lancets is between eight lancets and twelve lancets.

23. The lancet device of claim 20, wherein each of the plurality of lancets comprises a generally cylindrical portion.

24. The lancet device of claim 20, further comprising a cocking system for placing the lancet device in a trigger-set or armed position.

25. The lancet device of claim 20, further comprising a holding member which houses the plurality of lancets.

26. The lancet device of claim 20, wherein the plurality of lancets comprises a multi-lancet unit and further comprising a system, including the advance button, for removing or ejecting a lancet of the multi-lancet unit which is activated by the advance button.

27. The lancet device of claim 20, wherein the plurality of lancets comprises a multi-lancet unit and further comprising a manually activated system, including the advance button, for removing or ejecting a used lancet of the multi-lancet unit which is manually activated by the advance button.

28. The lancet device of claim 20, wherein the plurality of lancets comprises a multi-lancet unit and further comprising a lancet holding member locking system.

29. A method of puncturing a surface of skin using the lancet device of claim 20, the method comprising:
arranging the lancet device adjacent against a user's skin; and
triggering the lancet device so that one of the plurality of lancets is caused to penetrate the user's skin.

30. A lancet device comprising:
a trigger arranged on a sidewall and having a portion that can be contacted by a user;
a front cap mountable to a front portion of the sidewall and having a skin engaging surface with an opening allowing a lancet needle to pass therethrough;
a lock member movable to a position locking a holding member;
a releasable retaining member retaining the holding member in a trigger-set position;
a depth adjustment system;
a cocking system configured to place the lancet device is in a trigger-set position;
a multi-lancet unit comprising a plurality of lancets arranged one in front of the other and being insertable into the holding member as a unit; and an advancing system for axially moving or advancing the multi-lancet unit when the holding member is in a locked position.

31. A lancet device comprising:
a housing;
a trigger;
a cocking system configured to place the lancet device in a trigger-set or armed position;
the cocking system comprising a cocking member arranged in an area of a rear end of the housing;
a multi-lancet unit comprising a plurality of lancets arranged one in front of the other and positioned in the housing;
each lancet comprising a front end, a needle which extends from the front end, and a rear end;
a lancet holding member receiving therein the multi-lancet unit and being movable within the housing;
a retaining member holding the holding member in a trigger-set position;
the retaining member releasing the holding member when a user activates the trigger;
a lock member that is movable to a locking position and is so caused to move upon activation of a lancet ejection system and that prevents axial movement of the lancet holding member,
wherein the front end of at least one of the plurality lancets is removably connected to the rear end of another of the plurality of lancets.

32. A lancet device having lancet ejection and depth of penetration adjustment, comprising:
a housing;
a wall arranged in the housing and having an opening;
a rotatable depth of penetration adjustment member;
a trigger arranged on a side of the housing and being closer to a front end of the housing than to a rear end of the housing;
the trigger having a portion extending outside the housing so as to be contacted by a user;
a cocking system configured to place the lancet device in a trigger-set or armed position;
the cocking system comprising a cocking member arranged in an area of a rear end of the housing and having a portion extending into the housing and a portion extending outside the housing;
a lancet holding member axially movable within the housing and comprising:
  a rear portion arranged on a rear side of the wall;
  a front portion arranged on a front side of the wall;
  an opening arranged behind a front end of the lancet holding member;
  an integrally formed deflecting member; and
  a longitudinal length that is greater than a longitudinal length of the housing;
said deflecting member being configured to retain the lancet holding member in the trigger-set or armed position when in contact with a surface;
said deflecting member being movable upon activation of the trigger;
a first spring surrounding a portion of the lancet holding member and having a front end in contact with a portion of the lancet holding member;
a second spring arranged axially behind the first spring and surrounding another portion of the lancet holding member;
the second spring extending into a space disposed inside the cocking member;
a rear end of the lancet holding member being arranged axially in front of a rear end of the cocking member when the lancet device is in the trigger-set or armed position;
a slide arranged on a side of the housing and being closer to the front end of the housing than to the rear end of the housing;
the slide comprising:
  a portion disposed inside the housing;
  a portion extending outside the housing;
  a portion that can extend into the opening of the lancet holding member and contact a lancet; and
  a portion that can be slid forward to a position located in front of the front end of the housing,
wherein the lancet holding member is capable of moving between an initial position, the trigger-set or armed position, and a puncturing position.

33. The lancet device of claim 32, further comprising at least one of:
a front cover;
the rotatable depth of penetration adjustment member being arranged in the area of the rear end of the lancet device;
a lock member that is movable to a locking position that prevents axial movement of the lancet holding member, wherein, when the lock member is not in the locking position, the lancet holding member is capable of moving between the initial position, the trigger-set or armed position, and the puncturing position;
the slide comprising plural components;
a multi-lancet unit comprising a plurality of lancets arranged one in front of the other and positioned in the housing and each lancet comprising a front end, a needle which extends from the front end, and a rear end; and/or
a lock member that is movable to a locking position upon activation of the slide.

34. A lancet device having lancet ejection and depth of penetration adjustment, comprising:
a housing;
a wall arranged in the housing and having an opening;
the wall being arranged closer to a rear end of the housing than to a front end of the housing;
a front cover having a skin engaging surface and an opening allowing a needle of a lancet to pass therethrough during skin puncturing;
a trigger arranged on a side of the housing and being closer to the front end of the housing than to the rear end of the housing;
the trigger having a portion extending outside the housing so as to be contacted by a user;
a cocking system configured to place the lancet device in a trigger-set or armed position;
the cocking system comprising a cocking member arranged in an area of the rear end of the housing and having a portion extending into the housing and a portion extending outside the housing;
a lancet holding member axially movable within the housing and comprising:
  a rear portion arranged on a rear side of the wall;
  a front portion arranged on a front side of the wall;
  an opening arranged behind a front end of the lancet holding member;
  an integrally formed deflecting member; and
  a longitudinal length that is greater than a longitudinal length of the housing;

said deflecting member being configured to retain the lancet holding member in the trigger-set or armed position when in contact with a surface arranged in or on the housing;

said deflecting member being movable out of retaining engagement with the surface during triggering of the lancet device;

a first spring disposed in front of the wall and surrounding a portion of the lancet holding member;

a second spring disposed behind the wall, surrounding another portion of the lancet holding member, and extending into a space disposed inside the cocking member;

a rear end of the lancet holding member being arranged axially in front of a rear end of the cocking member when the lancet device is in the trigger-set or armed position;

a lancet ejector arranged on a side of the housing and being closer to the front end of the housing than to the rear end of the housing;

the lancet ejector comprising:
- a portion disposed inside the housing;
- a portion extending outside the housing;
- a portion that can extend into the opening of the lancet holding member and contact a lancet; and
- a portion that can be slid forward to a position located in front of the front end of the lancet holding member, wherein the lancet holding member is capable of moving between an initial position and a puncturing position, and wherein the lancet device is capable of assuming plural different depth of penetration adjustment positions.

35. The lancet device of claim 34, further comprising:

a lock member that is movable to a locking position that prevents axial movement of the lancet holding member; and a multi-lancet unit comprising a plurality of lancets arranged one in front of the other and positioned in the housing.

\* \* \* \* \*